United States Patent
Green et al.

(10) Patent No.: US 7,790,207 B2
(45) Date of Patent: *Sep. 7, 2010

(54) COLOUR REDUCTION IN CANOLA PROTEIN ISOLATE

(75) Inventors: Brent E. Green, Winnipeg (CA); Lei Xu, Ottawa (CA); Radka Milanova, Vancouver (CA); Kevin I. Segall, Winnipeg (CA)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 563 days.

This patent is subject to a terminal disclaimer.

(21) Appl. No.: 10/465,665

(22) Filed: Jun. 20, 2003

(65) Prior Publication Data

US 2004/0077838 A1    Apr. 22, 2004

Related U.S. Application Data

(60) Provisional application No. 60/389,957, filed on Jun. 20, 2002, provisional application No. 60/423,985, filed on Nov. 6, 2002.

(51) Int. Cl.
- *A61K 36/00* (2006.01)
- *A61K 47/00* (2006.01)
- *A61K 9/00* (2009.01)
- *A01N 65/00* (2006.01)

(52) U.S. Cl. .................. 424/776; 424/725; 424/400; 424/439

(58) Field of Classification Search .......... 530/370; 424/724, 400, 439, 442
See application file for complete search history.

(56) References Cited

U.S. PATENT DOCUMENTS

| 3,966,702 | A | * | 6/1976 | Carey | 530/378 |
| 4,158,656 | A | * | 6/1979 | Jones et al. | 530/377 |
| 4,169,090 | A | | 9/1979 | Murray | |
| 4,208,323 | A | | 6/1980 | Murray | |
| 4,285,862 | A | | 8/1981 | Murray | |
| 4,370,267 | A | | 1/1983 | Lehnhardt et al. | |
| 4,889,921 | A | * | 12/1989 | Diosady et al. | 530/377 |
| 5,844,086 | A | | 12/1998 | Murray | |
| 6,005,076 | A | * | 12/1999 | Murray | 530/377 |

FOREIGN PATENT DOCUMENTS

| DE | 2 322 462 A | 11/1974 |
| DE | 247 835 A | 7/1987 |
| DE | 100 35 292 A | 2/2002 |

OTHER PUBLICATIONS

Murray et al. "Rapeseed: a potential global source of high quality plant protein" Apr. 2001 pp. 30-34, XP002207606.
Database WPI, Section Ch, Derwent Publication Ltd., London, GB; XP002246020 & JP 05 04597 A. (Feb. 21, 1993).
Krzyzaniak A. et al., The Structure and properties of Napin-Seed Storage Protein from Rape vol. 42, No. ¾, 1998, pp. 201-204. XP000861830.

* cited by examiner

*Primary Examiner*—Christopher R Tate
*Assistant Examiner*—Randall Winston
(74) *Attorney, Agent, or Firm*—Sim & McBurney; Michael I. Stewart

(57) ABSTRACT

In the recovery of canola protein isolates from canola oil seeds steps are taken to inhibit the formation of coloring components and to reduce the presence of materials tending to form coloring components, to obtain a lighter and less yellow canola protein isolate.

6 Claims, No Drawings

COLOUR REDUCTION IN CANOLA PROTEIN ISOLATE

REFERENCE TO RELATED APPLICATIONS

This application claims priority pursuant to 35 USC 119(e) from copending U.S. Provisional Patents Applications Nos. 60/389,957 filed Jun. 20, 2002 and 60/432,985 filed Nov. 6, 2002.

FIELD OF INVENTION

The present invention relates to the recovery of canola protein isolate from canola seed meals.

BACKGROUND TO THE INVENTION

In U.S. Pat. Nos. 5,844,086 and 6,005,076 ("Murray II"), assigned to the assignee hereof and the disclosures of which are incorporated herein by reference, there is described a process for the isolation of protein isolates from oil seed meal having a significant fat content, including canola oil seed meal having such content. The steps involved in this process include solubilizing proteinaceous material from oil seed meal, which also solubilizes fat in the meal, and removing fat from the resulting aqueous protein solution. The aqueous protein solution may be separated from the residual oil seed meal before or after the fat removal step. The defatted protein solution then is concentrated to increase the protein concentration while maintaining the ionic strength substantially constant, after which the concentrated protein solution may be subjected to a further fat removal step. The concentrated protein solution then is diluted to cause the formation of a cloud-like mass of highly associated protein molecules as discrete protein droplets in micellar form. The protein micelles are allowed to settle to form an aggregated, coalesced, dense amorphous, sticky gluten-like protein isolate mass, termed "protein micellar mass" or PMM, which is separated from residual aqueous phase and dried.

The protein isolate has a protein content (as determined by Kjeldahl nitrogen or other convenient procedure N×6.25) of at least about 90 wt %, is substantially undenatured (as determined by differential scanning calorimetry) and has a low residual fat content. The term "protein content" as used herein refers to the quantity of protein in the protein isolate expressed on a dry weight basis. The yield of protein isolate obtained using this procedure, in terms of the proportion of protein extracted from the oil seed meal which is recovered as dried protein isolate was generally less than 40 wt %, typically around 20 wt %.

The procedure described in the aforementioned Murray II patent was developed as a modification to and improvement on the procedure for forming a protein isolate from a variety of protein source materials, including oil seeds, as described in U.S. Pat. No. 4,208,323 (Murray IB). The oil seed meals available in 1980, when U.S. Pat. No. 4,208,323 issued, did not have the fat contamination levels of the canola oil seed meals available at the time of the Murray II patents, and, as a consequence, the procedure of the Murray IB patent cannot produce from such oil seed meals, proteinaceous materials which have more than 90 wt % protein content. There is no description of any specific experiments in the Murray IB patent carried out using rapeseed (canola) meal as the starting material.

The Murray IB patent, itself was designed to be an improvement on the process described in U.S. Pat. Nos. 4,169,090 and 4,285,862 (Murray IA) by the introduction of the concentration step prior to dilution to form the PMM. The Murray IA patents describe one experiment involving rapeseed but provides no indication of the purity of the product. The concentration step described in the Murray IB patent served to improve the yield of protein isolate from around 20% for the Murray IA process.

One difficulty which the canola protein isolates produced by such prior procedures possess is a relatively dark yellow colour and an undesirable flavour. Phenolic compounds have been reported to be responsible for these problems of canola protein products including meal. Canola contains about ten times the quantity of phenolic compounds as is found in soybeans and may comprise sinapine and condensed tannins. Upon oxidation, phenolic compounds can give rise to the development of a dark colour. This problem is particularly acute with canola protein products produced by isoelectric precipitation where the strongly alkaline conditions lead to ready oxidation of phenolic compounds to quinones, which then react with the protein and impart a dark green or brown colour to the protein and solutions thereof. Other compounds and reactions also may contribute to colour formation.

SUMMARY OF INVENTION

The applicants provide herein an improvement in a process of forming a canola protein isolate wherein canola seeds are processed to form a canola protein meal, the canola protein meal is extracted to form an aqueous protein solution, the aqueous protein solution is concentrated, and the canola protein isolate is recovered from the concentrated aqueous protein solution.

Phenolic compounds are extracted from the canola meal in the extraction step and the quantity of free phenolics present can be extracted by UV absorbance at 330 nm (A330). Such phenolics are prone to oxidation to quinones and which react with proteins to form coloured compounds, which tend to absorb at higher wavelengths. Determination of absorbance at 420 nm (A420) provides a more direct measurement of actual visual yellow colouration of the isolate and canola protein solutions. In the present invention, during the processing to obtain the canola protein isolate, steps are taken to remove the phenolics so that they are unable to form visible colouring components, to inhibit oxidation of phenolics to visible colouring components and to remove other visible colouring components.

The improvement provided by one aspect of the present invention involves effecting at least one process step during the above-described process which results in a canola protein isolate having a decreased colour. The applicants have taken a multifaceted approach to this procedure and one or more of several steps may taken including:

processing of canola seed
    treatment of meal
    utilizing a specific form of canola protein meal
    effecting extraction of a canola protein under specific conditions
    processing of extract
    processing of the recovered canola protein isolate Two or more of such procedures may be employed and often combinations of such procedures are used.

Where the processing of seeds is effected, the procedure includes at least inactivation of myrosinase in the seeds while still hulled. By inactivating the myrosinase, any catalytic effect of the myrosinase on the breakdown of glucosinolates into the sulfur components which are anti-nutrients that contribute to taste and colour. The procedure is more fully described in copending U.S. patent application Ser. No.

10/871,065 filed Jun. 21, 2004, assigned to the assignee hereof and the disclosure of which is incorporated herein by reference.

The treatment of meal may involve extraction of the meal with a water miscible organic solvent including alcohols, such as ethanol, to extract phenolics and/or other colouring components.

Where a specific form of canola protein meal is used, such meal may be an air-desolventized meal, prepared by removing residual solvent from solvent extraction of canola oil seed meal at a temperature below about 50° C., generally at an ambient temperature of about 15° to about 30° C.

In addition, the specific form of canola protein meal may be a low-temperature toasted canola oil seed meal, prepared by removing residual solvent from solvent extraction of canola oil seed meal at an elevated temperature below about 100° C.

Where the process step involves the extraction step, the extraction step may be effected in the presence of an antioxidant to inhibit oxidation of phenolics and visible colour formation. Alternatively or in combination, the aqueous protein solution formed by the extraction step may be treated with at least one colouring component adsorbing agent. In addition, or alternatively, the treatment with at least one colouring component adsorbing agent may be effected on the concentrated canola protein solution formed in the concentration step.

Where the process step involves the concentration step, the concentrated aqueous canola protein solution is subject to diafiltration to wash colourants from the concentrated canola protein solution. The diafiltration may be carried out using an aqueous solution containing an antioxidant to inhibit oxidation of phenolics and visible colour formation during the diafiltration.

Where the process step involves the recovered canola protein isolate, the process step may involve extraction of the canola protein isolate using aqueous alcoholic solutions, such as aqueous ethanol, to extract phenolics and/or visible colourants from the canola protein isolate.

The canola protein isolate may be recovered from the concentrated aqueous protein solution by adding the concentrated aqueous solution to chilled water to form a protein micellar mass, and separating the protein micellar mass from supernatant.

The supernatant may be processed to recover additional canola protein isolate therefrom by concentrating the supernatant, subjecting the concentrated supernatant to diafiltration to remove phenolics and/or visible colorants from the concentrated supernatant and then recovering the canola protein isolate from the diafiltered supernatant, such as by drying the diafiltered supernatant.

By preventing colour formation and by improving the colour of the canola protein isolate, the product may be used in a wider range of applications. The removal and prevention of the formation of colourants in accordance with this invention is thought also to improve the flavour of the canola protein isolates.

The protein isolate produced according to the process herein may be used in conventional applications of protein isolates, such as, protein fortification of processed foods, emulsification of oils, body formers in baked goods and foaming agents in products which entrap gases. In addition, the protein isolate may be formed into protein fibers, useful in meat analogs, may be used as an egg white substitute or extender in food products where egg white is used as a binder. The canola protein isolate may be used as nutritional supplements. Other uses of the canola protein isolate are in pet foods, animal feed and in industrial and cosmetic applications and in personal care products.

In accordance with one specific aspect of the present invention, there is provided a process of preparing a canola protein isolate from canola oil seed meal, which comprises (a) extracting the canola oil seed meal and to cause solubilization of the protein in the canola oil seed meal to form an aqueous protein solution having a pH of about 5 to about 6.8 by using an aqueous salt solution containing an antioxidant, (b) separating the aqueous protein solution from residual oil seed meal, (c) increasing the protein concentration of said aqueous protein solution while maintaining the ionic strength substantially constant by use of a selective membrane technique to provide a concentrated protein solution, (d) diluting said concentrated protein solution into chilled water having a temperature of below about 15° C. to cause the formation of discrete protein micelles in the aqueous phase, (e) settling the protein micelles to form an amorphous, sticky, gelatinous, gluten-like protein micellar mass, and (f) recovering the protein micellar mass from supernatant, the protein micellar mass having a protein content of at least about 90 wt % (N×6.25) on a dry weight basis.

In accordance with another specific aspect of the present invention, there is provided a process of preparing a canola protein solution from canola oil seed meal, which comprises (a) washing said canola oil seed meal with an alcohol, (b) extracting the washed canola oil seed meal to cause solubilization of the protein in the washed canola oil seed meal to form an aqueous protein solution having a pH of about 5 to about 6.8, (c) separating the aqueous protein solution from residual oil seed meal, (d) increasing the protein concentration of said aqueous protein solution while maintaining the ionic straight substantially constant by use of a selective membrane technique to provide a concentrated protein solution, (e) diluting said concentrated protein solution into chilled water having a temperature of below about 15° C. to cause the formation of discrete protein micelles in the aqueous phase, (f) settling the protein micelles to form an amorphous, sticky, gelatinous, gluten-like protein micellar mass, and (g) recovering the protein micellar mass from supernatant, the protein micellar mass having a protein content of at least about 90 wt % (N×6.25) on a dry weight basis.

In accordance with a further specific aspect of the present invention, three s provided a process of preparing a canola protein isolate from canola oil seed meal, which comprises (a) extracting the canola oil seed meal to cause solubilization of the protein in the canola oil seed meal to form an aqueous protein solution having a pH about 5 to about 6.8, (b) separating the aqueous protein solution from residual oil seed meal, (c) increasing the protein concentration of said aqueous protein solution while maintaining the ionic strength substantially constant by effecting ultrafiltration of the aqueous protein solution to provide a concentrated protein solution, (d) subjecting the concentrated protein solution to diafiltration, (e) diluting the diafiltered protein solution into chilled water having a temperature below about 15° C. to cause the formation of discrete protein micelles in the aqueous phase, (f) settling the protein micelles to form an amorphous, sticky, gelatinous, gluten-like protein micellar mass, and (g) recovering the protein micellar mass from supernatant, the protein micellar mass having a protein content of at least about 90 wt % (N×6.25) on a dry weight basis.

In accordance with a yet further aspect of the present invention, there s provided a process of preparing a canola protein isolate from canola oil seed meal, which comprises (a) extracting the canola oil seed meal to cause solubilization of the protein in the canola oil seed meal to form an aqueous protein solution having a pH of about 5 to about 6.8, (b) separating the aqueous protein solution from the residual oil seed meal, (c) increasing the protein concentration of said aqueous protein solution while maintaining the ionic strength substantially constant by use of a selective membrane technique to form a concentrated protein solution, (d) diluting said concentrated protein solution into chilled water having a temperature below about 15° C. to cause the formation of discrete protein micelles in the aqueous phase, (e) settling the protein micelles to form an amorphous, sticky, gelatinous, gluten-like protein micellar mass, (f) separating the protein micellar mass from supernatant, (g) drying the protein micellar mass to provide a canola protein isolate having a protein content of at least about 90 wt % (N×6.25) on a dry weight basis, and (h) extracting said canola protein isolate with an aqueous alcoholic solution.

In accordance with an additional aspect of the present invention, three is provided a process of preparing a canola protein isolate from canola oil seed meal, which comprises (a) extracting the canola oil seed meal to cause solubilization of the protein in the canola oil seed meal to form an aqueous protein solution having a pH of about 5 to about 6.8, (b) separating the aqueous protein solution from residual oil seed meal, (c) increasing the protein concentration of said aqueous protein solution while maintaining the ionic strength substantially constant by use of a selective membrane technique to provide a concentrated protein solution, (d) pasteurizing the concentrated protein solution to form a pasteurized protein solution, (e) diluting the pasteurized protein solution into chilled water having a temperature below about 15° C. to cause the formation of discrete protein micelles in the aqueous phase, (f) settling the protein micelles to form an amorphous, sticky, gelatinous, gluten-like protein micellar mass, and (g) recovering the protein micellar mass from supernatant, the protein micellar mass having a protein content of at least about 90 wt % (N×6.25) on a dry weight basis.

In accordance with another aspect of the present invention, there is provided a process of preparing a canola protein isolate from canola oil seed, which comprises (a) treating canola oil seeds to inactivate myrosinases contained in the oil seeds to produce treated oil seeds, (b) processing said oil seeds to remove canola oil therefrom and produce a canola oil seed meal, (c) extracting the canola oil seed to cause solubilization of the protein in the canola oil seed to form an aqueous solution having a pH of about 5 to about 6.8, (d) separating the aqueous protein solution from residual oil seed meal, (e) increasing the protein concentration of said aqueous protein solution which maintaining the ionic strength substantially constant by use of a selective membrane technique to provide a concentrated protein solution, (f) diluting the concentrated protein solution into chilled water having a temperature below about 15° C. to cause formation of discrete protein micelles in the aqueous phase, (g) settling the protein micelles to form an amorphous, sticky, gelatinous, gluten-like protein micellar mass, and (h) recovering the protein micellar mass from supernatant, the protein micellar mass having a protein content of at least about 90 wt % of (N×6.25) on a dry weight basis.

Canola is also known as rapeseed or oil seed rape.

GENERAL DESCRIPTION OF INVENTION

Colour improvement may be achieved by the processing of seeds. Hulled seeds are subjected to heat inactivation of myrosinase using steam. The inactivated seeds then may be processed in conventional manner to recover oil from the seeds and to form canola oil seed meal.

It is preferred, in accordance with one embodiment of the invention, for the oil seed meal to be desolventized by toasting at an elevated temperature below about 100° C., since such meal gives rise to less colour development than meal desolventized using conventional, much higher, toasting temperatures. The formation of a canola protein isolate having a protein content of at least about 90 wt % (N×6.25), preferably at least about 100 wt %, from such meal is described in copending U.S. patent application Ser. No. 10/314,202 filed Dec. 9, 2002, assigned to the assignee hereof and the disclosure of which is incorporated herein by reference.

More preferably, the oil seed meal is desolventized in air at temperatures below about 50° C., preferably around ambient temperature about 15° to about 30° C., since even less colour than in the case of the use of the toasted meal is present in the extract solution. The formation of a canola protein isolate having a protein content of at least about 90 wt % (N×6.25), preferably at least about 100 wt %, from such meal is described in copending U.S. applications Nos. 60/390,126 filed Jun. 21, 2002 and 60/401,712 filed Aug. 8, 2002 and Ser. No. 10/465,238 filed Jun. 20, 2003, assigned to the assignee hereof and the disclosures of which are incorporated herein by reference.

Canola protein isolates can be formed from canola oil seed meal. In copending U.S. Patent Applications Nos. 60/288,415 filed May 4, 2001, 60/326,987 filed Oct. 5, 2001, 60/331,066 filed Nov. 7, 2001, 60/333,494 filed Nov. 26, 2001, 60/374,801 filed Apr. 24, 2002 and Ser. No. 10/137,391 filed May 3, 2002 (WO 02/089597), all assigned to the assignee hereof and the disclosures of which are incorporated herein by reference, there is described a method of making canola protein isolates from canola oil seed meal, such isolates having at least about 100 wt % protein content (N×6.25). The procedure involves a multiple step process comprising extracting canola oil seed meal using a salt solution, separating the resulting aqueous protein solution from residual oil seed meal, increasing the protein concentration of the aqueous solution to at least about 200 g/L while maintaining the ionic strength substantially constant by using a selective membrane technique, diluting the resulting concentrated protein solution into chilled water to cause the formation of protein micelles, settling the protein micelles to form an amorphous, sticky, gelatinous gluten-like protein micellar mass (PMM), and recovering the protein micellar mass from supernatant having a protein content of at least about 100 wt % (N×6.25). As used herein, protein content is determined on a dry weight basis. The recovered PMM may be dried.

In one embodiment of the process described above and as specifically described in U.S. Patent Applications Nos. 60/326,987, 60/331,066, 60/333,494, 60/374,801 and Ser. No. 10/137,391, the supernatant from the PMM settling step is processed to recover a protein isolate comprising dried protein isolate from the wet PMM and supernatant. This procedure may be effected by initially concentrating the supernatant using ultrafiltration membranes, mixing the concentrated supernatant with the wet PMM and drying the mixture. The resulting canola protein isolate has a high purity of at least about 90 wt % of protein (N×6.25), preferably at least about 100 wt % protein (N×6.25).

In another embodiment of the process described above and as specifically described in Applications Nos. 60/333,494, 60/374,801 and Ser. No. 10/137,391, the supernatant from the PMM settling step is processed to recover a protein isolate from the supernatant. This procedure may be effected by initially concentrating the supernatant using ultrafiltration membranes and drying the concentrate. The resulting canola protein isolate has a high purity of at least about 90 wt % protein (N×6.25), preferably at least about 100 wt % protein (N×6.25).

The procedures described in the aforementioned U.S. patent applications are essentially batch procedures. In copending U.S. Patent Applications Nos. 60/331,646 filed Nov. 20, 2001, 60/383,809 filed May 30, 2002 and Ser. No. 10/298,678 filed Nov. 19, 2002 (WO 03/043439), assigned to the assignee hereof and the disclosures of which are incorporated herein by reference, there is described a continuous process for making canola protein isolates. In accordance therewith, canola oil seed meal is continuously mixed with a salt solution, the mixture is conveyed through a pipe while extracting protein from the canola oil seed meal to form an aqueous protein solution, the aqueous protein solution is continuously separated from residual canola oil seed meal, the aqueous protein solution is continuously conveyed through a selective membrane operation to increase the protein content of the aqueous protein solution to at least about 200 g/L while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is removed from the settling vessel and may be dried. The PMM has a protein content of at least about 90 wt % (N×6.25), preferably at least about 100 wt % (N×6.25).

As described in the aforementioned U.S. Patent Applications Nos. 60/326,987, 60/331,066, 60/333,494, 60/333,494, 60/374,801 and Ser. No. 10/137,391, the overflowed supernatant may be processed to recover canola protein isolate therefrom.

In accordance with one embodiment of the present invention, the oil seed meal may initially be solvent extracted to remove phenolics and colourants therefrom. Such solvent extraction may be effected using a water-soluble organic solvent for phenolics and/or visible colourants, such as a water-soluble alcohol, preferably ethanol.

The extraction may be effected by dispersing the canola oil seed meal in the solvent at a w/v ratio of about 1:3 to about 1:10, preferably about 1:5. The slurry may be stirred for about 5 to about 60 minutes, preferably about 15 to about 30 minutes, at a temperature of about 15° to about 45° C., preferably about 30° to about 35° C. One suitable set of conditions is a 30 minutes extraction at 35° C. Such extraction may be effected a multiple number of times until no additional phenolics and/or visible colour are extracted.

In the process of the present invention, proteinaceous material is solubilized from canola oil seed meal. The proteinaceous material may be the protein naturally occurring in canola seed or the proteinaceous material may have been modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The processing of seed, when effected for the removal of canola oil from canola oil seed usually is effected as a separate operation from the protein isolate recovery procedure of the present invention described herein.

Protein solubilization is effected most efficiently by using a food grade salt solution since the presence of the salt enhances the removal of soluble protein from the oil seed meal. Where the canola protein isolate is intended for non-food uses, non-food-grade chemicals may be used. The salt usually is sodium chloride, although other salts, such as, potassium chloride, may be used. The salt solution has an ionic strength of at least about 0.10, preferably at least about 0.15, to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the oil seed meal chosen. The food grade salt solution may have an ionic strength ranging up to about 0.25.

In view of the greater degree of dilution required for protein precipitation with increasing ionic strengths, it is usually preferred to utilize an ionic strength value less than about 0.8, and more preferably a value of about 0.15 to about 0.6.

In a batch process, the salt solubilization of the protein is effected at a temperature of at least about 5° C. and preferably up to about 35° C., preferably accompanied by agitation to decrease the solubilization time, which is usually about 10 to about 60 minutes. It is preferred to effect the solubilization to extract substantially as much protein from the oil seed meal as is practicable, so as to provide an overall high product yield.

The lower temperature limit of about 5° C. is chosen since solubilization is impractically slow below this temperature while the upper preferred temperature limit of about 35° C. is chosen since the process becomes uneconomic at higher temperature levels in a batch mode.

In a continuous process, the extraction of the protein from the canola oil seed meal is carried out in any manner consistent with effecting a continuous extraction of protein from the canola oil seed meal. In one embodiment, the canola oil seed meal is continuously mixed with a food grade salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially as much protein from the canola oil seed meal as is practicable. The solubilization in the continuous procedure preferably is effected at elevated temperatures, preferably above about 35° C., generally up to about 65° C. or more.

The aqueous food grade salt solution and the canola oil seed meal have a natural pH of about 5 to about 6.8 to enable a protein isolate to be formed by the micellar route, as described in more detail below.

At and close to the limits of the pH range, protein isolate formation occurs only partly through the micelle route and in lower yields than attainable elsewhere in the pH range. For these reasons, mildly acidic pH values of about 5.3 to about 6.2 are preferred.

The pH of the salt solution may be adjusted to any desired value within the range of about 5 to about 6.8 for use in the extraction step by the use of any convenient acid, usually hydrochloric acid, or alkali, usually sodium hydroxide, as required.

The concentration of oil seed meal in the food grade salt solution during the solubilization step may vary widely. Typical concentration values are about 5 to about 15% w/v.

In accordance with one embodiment of the invention, an antioxidant may be present in the food grade salt solution to inhibit oxidation of phenols in the canola oil seed meal to components which react with the protein and cause colour darkening. Any desired food-grade antioxidant may be used, such as sodium sulfite and ascorbic acid. The quantity of antioxidant employed in the aqueous food grade salt solution depends on the material employed and may vary from about 0.01 to about 1 wt %, preferably about 0.05 to about 0.1 wt %. Inhibition of oxidation of phenolics by the use of antioxidants results in reduced extract colour (absorbance at 420 nm) while the concentration of phenolics (absorbance at 330 nm) remains largely unchanged.

In the presence of added sodium sulfite, even at a salt concentration as low as 0.05 M, the protein concentration in the extract at pH 6.3 was comparable with that with 0.15 M salt but without sodium sulfite.

The protein solution resulting from the extraction step generally has a protein concentration of about 5 to about 40 g/L, preferably about 10 to about 30 g/L.

In choosing the parameters of the extraction step, the desire to extract as much protein from the canola oil seed meal as is possible is balanced with the desire to minimize the colour of the resulting extract solution. In considering the data presented herein, an extraction time of 30 minutes generally is sufficient to extract all the protein that is going to be extracted under the prevailing pH and salt molarity. A higher pH increases the amount of protein extracted and results in a protein solution which is visibly darker in colour (as measured by absorbance at A420).

It is possible to extract as much protein in 10 minutes with 0.1 M saline at pH 8.0 as is extracted with 0.15 M saline at pH 6.3 in 30 minutes. There is a marked decrease in the A330 at extraction at pH 9.8 when compared to extraction with lower pH, although the colour is visibly darker as the pH increases. An explanation for this phenomenon may be that the phenolics are reacting to form yellow colorants that do not absorb at A330, but rather absorb at higher values between A360 and A400. For those reasons, extraction of the canola protein meal is effected at a pH below 8.

The aqueous phase resulting from the extraction step then may be separated from the residual canola meal, in any convenient manner, such as by employing vacuum filtration, followed by centrifugation and/or filtration to remove residual meal. The separated residual meal may be dried for disposal.

Where the canola seed meal contains significant quantities of fat, as described in the Murray II patents, then the defatting steps described therein may be effected on the separated aqueous protein solution and on the concentrated aqueous protein solution discussed below.

As an alternative to extracting protein from the canola oil seed meal with an aqueous salt solution, such extraction may be made using water alone, although the utilization of water alone tends to extract less protein from the canola oil seed meal than the aqueous salt solution. Where such alternative is employed, then the salt, in the concentrations discussed above, may be added to the protein solution after separation from the residual oil seed meal in order to maintain the protein in solution during the concentration step described below. When a first fat removal step is carried out, the salt generally is added after completion of such operation.

Another alternative procedure is to extract the canola oil seed meal with a food grade salt solution at a relatively high pH value above about 6.8, generally up to about 11. However, as noted above, extraction at pH values greater than about 8 generally are avoided since considerable visible colour formation results at such pH values. The pH of the food grade salt solution, may be adjusted in pH to the desired alkaline value by the use of any convenient food-grade alkali, such as aqueous sodium hydroxide solution. Alternatively, the protein may be extracted from the canola oil seed meal with the salt solution at a relatively low pH below about pH 5, generally down to about pH 3. Where such alternative is employed, the aqueous phase resulting from the canola oil seed meal extraction step then is separated from the residual canola meal, in any convenient manner, such as by employing vacuum filtration, followed by centrifugation and/or filtration to remove residual meal. The separated residual canola meal may be dried for disposal.

The aqueous protein solution resulting from the high or low pH extraction step then may be pH adjusted to the range of about 5 to about 6.8, preferably about 5.3 to about 6.2, as discussed above, prior to further processing to recover canola protein isolate mainly by the micelle route, as discussed below. Such pH adjustment may be effected using any convenient acid, such as hydrochloric acid, or alkali, such as sodium hydroxide, as appropriate.

Following extraction of the protein, the protein solution may be subjected to one or more colour removal steps, in accordance with another embodiment of the invention, including ultrafiltration/diafiltration and contact with a colour adsorbing agent. In the ultrafiltration step, the protein content of the aqueous protein solution is increased while the salt concentration remains unchanged. The ultrafiltration may be effected using membranes having a molecular weight cut-off consistent with permitting phenolics and colouring agents to pass through the membrane with the permeate while the protein is retained, typically an ultrafiltration membrane having a molecular weight cut-off of about 3,000 to about 50,000 daltons, preferably about 5000 to about 10,000 daltons, having regard to differing membrane materials and configurations. The membranes may be hollow-fibre membranes or spiral-wound membranes. For continuous operation, the membranes may be dimensioned to permit the desired degree of concentration as the aqueous protein solution passes through the membranes.

The protein solution is concentrated by the ultrafiltration step from about 4 to about 20 fold and preferably is effected to provide a concentrated protein solution having a protein concentration of at least about 200 g/L, more preferably at least about 250 g/L.

The concentrated protein solution then is subjected to a diafiltration step using an aqueous salt solution of the same molarity and pH as the extraction solution. Such diafiltration may be effected using from about 2 to about 20 volumes of diafiltration solution, preferably about 5 to about 10 volumes of diafiltration solution. In the diafiltration operation, further quantities of phenolics and visible colour are removed from the aqueous protein solution by passage through the membrane with the permeate. The diafiltration operation may be effected until no significant further quantities of phenolics and visible colour are present in the permeate. Such diafiltration may be effected using a membrane having a molecular weight cut-off in the range of about 3000 to about 50,000 daltons, preferably about 5,000 to about 10,000 daltons, having regard to different membrane materials and configuration.

In accordance with an aspect of this embodiment of the invention, an antioxidant may be present in the diafiltration medium using at least part of the diafiltration step. The antioxidant may be any convenient food grade antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentration step and the diafiltration step may be effected at any convenient temperature, generally about 20° to about 60° C., and for the period of time to effect the desired degree of concentration. The temperature and other conditions used to some degree depend upon the membrane equipment used to effect the concentration and the desired protein concentration of the solution.

In effecting the ultrafiltration/diafiltration operations, the conditions are chosen having in mind the desire to provide a protein solution having the highest protein concentration and lowest colour. Based on the experiments reported below, the ultrafiltration/diafiltration (UF/DF) procedure is able to effectively reduce A330 values (phenolics concentration) by about 28% to about 74%, depending on pH and saline content. The ultrafiltration/diafiltration operations also have the effect of removing anti-nutritional factors, thereby improving the nutritional quality of the canola protein isolate.

The UF/DF permeates had the highest A330 values at pH 8.0 and 6.3. These high permeate A330 values are likely due to unbound phenolics being able to pass through the membranes into the permeate while at pH 9.8 and pH 11.0, the phenolics have reacted to form colourants and do not absorb as strongly at A330.

Extractions effected at higher pH and saline level had the highest starting A330 readings and in most cases the lowest final retentate A330 readings. At the higher pH and saline values, permeates contained higher levels of nitrogen, indicating protein loss.

A330 to protein ratios for final retentate indicate that the best ratios are achieved at pH values from pH 6.3 and 8.0, indicating that less A330 component per protein than the higher pH tests and a more effective removal by the UF/DF procedures. In all but 0 M and 0.25 M saline concentrations, pH 6.3 had the best A330 to protein ratio. Having regard thereto, pH 6.3 appears to be the best pH level tested for diafiltering colour out of the protein solution with 0.25 M saline being the best salt level for providing the highest protein level.

The ultrafiltration/diafiltration operations may be followed by treatment with a pigment adsorbing agent. In the aforementioned copending U.S. Patent Applications Nos. 60/288,415, 60/326,987, 60/331,066, 60/333,494, 60/374,801 and Ser. No. 10/137,391 (WO 02/089597), there is described the use of powdered activated carbon to effect colour reduction.

As described in such applications, such colour reduction step is carried out on the canola protein solution prior to concentration and results in a lighter colour and less intense yellow in the product canola protein isolate compared to the absence of such step. In accordance with another embodiment of the present invention, the use of colour component adsorbing materials is preferably effected on the concentrated and diafiltered canola protein solution. Powdered activated carbon may be used herein as well as granulated activated carbon (GAC). Another material which may be used as a colour adsorbing agent is polyvinyl pyrrolidone. Alternatively, in accordance with another embodiment of the invention, the use of colour component adsorbing materials may be effected on the canola protein solution prior to ultrafiltration and optional diafiltration, and/or directly in the extraction step. When the colour adsorbing material is employed prior to the ultrafiltration step, diafiltration may be omitted, in the event such diafiltration does not remove any additional phenolics and/or visible colour.

In the experiments described below, polyvinyl pyrrolidone and GAC reduced A330 values better at pH 6.3 and 8.0 than at pH 9.8 and 11, probably due to binding of quinones to protein at the two higher pH levels. Polyvinyl pyrrolidone produced a good reduction in A330 without protein loss. Other potential materials tested were unsatisfactory, either as a result of unacceptable protein losses or an inability to reduce the A330 of the solution.

The colour absorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinylpyrrolidone is used as the colour adsorbing agent, an amount of about 0.5 to about 5 w/v, preferably about 2 to about 3% w/v, may be used. The colour adsorbing agent may be removed from the canola protein solution by any convenient means, such as by filtration.

Following completion of the treatment by colour adsorbing agent on diafiltered canola protein solution, the resulting protein solution is processed to produce a canola protein isolate therefrom. The recovery of the canola protein isolate may be effected in any convenient manner, depending on the parameters of the protein solution.

For example, the canola protein isolate may be recovered by isoelectric precipitation from alkaline solutions or by a protein micellar mass process from more neutral solutions. Alternatively, the protein may be precipitated by increasing the salt concentration.

The processing of the canola protein solution to recover a canola protein isolate preferably is carried out using a protein micellar mass process as described in the aforementioned U.S. patent applications and in more detail below, since the extraction pH conditions lead to less colour formation than those employed for the isoelectric precipitation techniques.

Depending on the temperature employed in the colour removal steps carried out on the aqueous canola protein solution, the concentrated protein solution may be warmed to a temperature of at least about 20°, and up to about 60° C., preferably about 25° to about 40° C., to decrease the viscosity of the concentrated, optionally diafiltered, protein solution to facilitate performance of the subsequent dilution step and micelle formation. The concentrated and optionally diafiltered protein solution should not be heated beyond a temperature above which the temperature of the concentrated and optionally diafiltered protein solution does not permit micelle formation on dilution by chilled water. The concentrated and optionally diafiltered protein solution may be subject to a further defatting operation, if required, as described in the Murray II patents.

The concentrated protein solution resulting from the colour removal steps may be subjected to pasteurization to kill any bacteria which may have been present in the original meal as a result of storage or otherwise and extracted from the meal into the canola protein isolate solution in the extraction step. Such pasteurization may be effected under any desired pasteurization conditions. Generally, the concentrated and optionally diafiltered protein solution is heated to a temperature of about 55° to about 70° C., preferably about 60° to about 65° C., for about 10 to about 15 minutes, preferably about 10 minutes. The pasteurized concentrated protein solution then may be cooled for further processing as described below, preferably to a temperature of about 25° to about 40° C.

The concentrated protein solution resulting from the colour removal steps and optional defatting and pasteurization steps then is diluted to effect micelle formation by mixing the concentrated protein solution with chilled water having the volume required to achieve the degree of dilution desired. Depending on the proportion of canola protein desired to be obtained by the micelle route and the proportion from the supernatant, the degree of dilution of the concentrated protein solution may be varied. With higher dilution levels, in general, a greater proportion of the canola protein remains in the aqueous phase.

When it is desired to provide the greatest proportion of the protein by the micelle route, the concentrated protein solution is diluted by about 15 fold or less, preferably about 10 fold or less.

The chilled water with which the concentrated protein solution is mixed has a temperature of less than about 15° C., generally about 3° to about 15° C., preferably less than about 10° C., since improved yields of protein isolate in the form of protein micellar mass are attained with these colder temperatures at the dilution factors used.

In a batch operation, the batch of concentrated protein solution is added to a static body of chilled water having the desired volume, as discussed above. The dilution of the concentrated protein solution and consequential decrease in ionic strength causes the formation of a cloud-like mass of highly associated protein molecules in the form of discrete protein droplets in micellar form. In the batch procedure, the protein micelles are allowed to settle in the body of chilled water to form an aggregated, coalesced, dense, amorphous, sticky, gluten-like protein micellar mass (PMM). The settling may be assisted, such as by centrifugation. Such induced settling decreases the liquid content of the protein micellar mass, thereby decreasing the moisture content generally from about 70% by weight to about 95% by weight to a value of generally about 50% by weight to about 80% by weight of the total micellar mass. Decreasing the moisture content of the micellar mass in this way also decreases the occluded salt content of the micellar mass, and hence the salt content of dried isolate.

Alternatively, the dilution operation may be carried out continuously by continuously passing the concentrated protein solution to one inlet of a T-shaped pipe, while the diluting water is fed to the other inlet of the T-shaped pipe, permitting mixing in the pipe. The diluting water is fed into the T-shaped pipe at a rate sufficient to achieve the desired degree of dilution.

The mixing of the concentrated protein solution and the diluting water in the pipe initiates the formation of protein micelles and the mixture is continuously fed from the outlet from the T-shaped pipe into a settling vessel, from which, when full, supernatant is permitted to overflow. The mixture preferably is fed into the body of liquid in the settling vessel in a manner which minimizes turbulence within the body of liquid.

In the continuous procedure, the protein micelles are allowed to settle in the settling vessel to form an aggregated, coalesced, dense, amorphous, sticky, gluten-like protein micellar mass (PMM) and the procedure is continued until a desired quantity of the PMM has accumulated in the bottom of the settling vessel, whereupon the accumulated PMM is removed from the settling vessel.

The combination of process parameters of concentrating the protein solution to a protein content of at least about 200 g/L and the use of a dilution factor less than about 15, result in higher yields, often significantly higher yields, in terms of recovery of protein in the form of protein micellar mass from the original meal extract, and much purer isolates in terms of protein content than achieved using any of the known prior art protein isolate forming procedures discussed in the aforementioned US patents.

The settled isolate is separated from the residual aqueous phase or supernatant, such as by decantation of the residual aqueous phase from the settled mass or by centrifugation. The PMM may be used in the wet form or may be dried, by any convenient technique, such as spray drying, freeze drying or vacuum drum drying, to a dry form. The dry PMM has a high protein content, in excess of about 90 wt % protein, preferably at least about 100 wt % protein (calculated as N×6.25), and is substantially undenatured (as determined by differential scanning calorimetry). The dry PMM isolated from fatty oil seed meal also has a low residual fat content, when the procedures of the Murray II patents are employed, which may be below about 1 wt %.

The supernatant from the PMM formation and settling step contains significant amounts of canola protein, not precipitated in the dilution step, and is processed to recover canola protein isolate therefrom. The supernatant from the dilution step, following removal of the PMM, is concentrated to increase the protein concentration thereof. Such concentration is effected using any convenient selective membrane technique, such as ultrafiltration, using membranes with a suitable molecular weight cut-off permitting low molecular weight species, including the salt and other non-proteinaceous low molecular weight materials extracted from the protein source material, to pass through the membrane, while retaining canola protein in the solution. Ultrafiltration membranes having a molecular weight cut-off of about 3000 to 10,000 daltons, having regard to differing membrane materials and configuration, may be used. Concentration of the supernatant in this way also reduces the volume of liquid required to be dried to recover the protein. The supernatant generally is concentrated to a protein concentration of about 100 to about 400 g/L, preferably about 200 to about 300 g/L, prior to drying. Such concentration operation may be carried out in a batch mode or in a continuous operation, as described above for the protein solution concentration step.

In accordance with another embodiment of the invention, prior to drying, the concentrated supernatant is subjected to a diafiltration step using water. Such diafiltration may be effected using about 2 to about 20 volumes of diafiltration solution, preferably about 5 to about 10 volumes of diafiltration solution. In the diafiltration operation, further quantities of phenolics and visible colour are removed from the concentrated supernatant by passage through the membrane with the permeate. The diafiltration operation may be effected until no significant further quantities of phenolics and visible colour are removed in the permeate. Such diafiltration may be effected using a membrane having a molecular weight cut-off in the range of about 3000 to about 50,000 daltons, preferably about 5000 to about 10,000 daltons, having regard to different membrane materials and configurations.

In accordance with an aspect of this embodiment of the invention, an antioxidant may be present in the diafiltration medium. The antioxidant may be any convenient food grade antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentrated supernatant may be used in the wet form or may be dried by any convenient technique, such as spray drying, freeze drying or vacuum drum drying, to a dry form to provide a further canola protein isolate. Such further canola protein isolate has a high protein content, in excess of about 90 wt %, preferably at least about 100 wt % protein (calculated as N×6.25) and is substantially undenatured (as determined by differential scanning calorimetry).

If desired, at least a portion of the wet PMM may be combined with at least a portion of the concentrated supernatant prior to drying the combined protein streams by any convenient technique to provide a combined canola protein isolate composition according to one embodiment of the invention. The relative proportions of the proteinaceous materials mixed together may be chosen to provide a resulting canola protein isolate composition having a desired profile of 2S/7S/12S proteins. Alternatively, the dried protein isolates may be combined in any desired proportions to provide any desired specific 2S/7S/12S protein profiles in the mixture. The combined canola protein isolate composition has a high protein content, in excess of about 90 wt %, preferably at least about 100 wt %, (calculated as N×6.25) and is substantially undenatured (as determined by differential scanning calorimetry).

In another alternative procedure, where a portion only of the concentrated supernatant is mixed with a part only of the PMM and the resulting mixture dried, the remainder of the concentrated supernatant may be dried as may any of the remainder of the PMM. Further, dried PMM and dried supernatant also may be dry mixed in any desired relative proportions, as discussed above.

By operating in this manner, a number of canola protein isolates may be recovered, in the form of dried PMM, dried supernatant and dried mixtures of various proportions by weight of PMM-derived canola protein isolate and supernatant-derived canola protein isolate, generally from about 5:95 to about 95:5 by weight, which may be desirable for attaining differing functional and nutritional properties based on the differing proportions of 2S/7S/12S proteins in the compositions.

In accordance with another embodiment of the invention, PMM-derived canola protein isolate and the supernatant-derived canola protein isolate may be treated to remove colour-imparting components thereof. Such treatment conveniently is effected using a water-miscible organic solvent for phenolics and/or visible colourants in mixture with water.

Since water-miscible organic solvent may be an alcohol. Preferred is a blend of ethanol and water, generally in a volume ratio of about 2:1 to about 1:2, preferably 1:1. The canola protein isolate is dispersed in the solvent blend in an amount of about 5 to about 25% w/v, preferably about 8 to about 23% w/v, generally at ambient temperature. The slurry of canola protein isolate may be mixed for about 30 to about 60 minutes, preferably about 30 minutes. Following the extraction period, the slurry is settled, such as by centrifugation, and the canola protein isolate is recovered. The extraction may be repeated, if desired, until no additional phenolics and/or visible colourants are removed. The canola protein isolate may be redispersed in an alcohol, such as ethanol, to remove water from the isolate, which then may be separated and dried.

EXAMPLES

Example 1

This Example shows the effect of various parameters on protein extraction and protein solution colour.

A series of experimental runs was performed in which 37.5 g of commercial canola meal (AL-016) was mixed with water containing NaCl of desired concentration at the desired pH, at a meal concentration of 7.5% w/v at 20° C. Sodium chloride concentrations employed were 0, 0.05, 0.10, 0.15 and 0.25 M and pH values used were pH 6.3, 8.0, 9.8 and 11.0. A sample of about 30 mL of extract was taken every 10 minutes during the 60 minutes extraction period and centrifuged at 10,000×g for 5 minutes. The supernatant of each sample was analyzed for protein concentration at the end of the extraction period. The entire batch was centrifuged at 10,000×g for fifteen minutes and the supernatant was vacuum filtered using a 0.45 μm micro filter. The filtered supernatant was analyzed for protein content and for free phenolics concentration (absorbance at 330 nm).

A 100 ml aliquot was drawn from the clarified supernatant for ultrafiltration (UF) by a concentration factor of 4 using an Amicon 8400 unit with a membrane of 10,000 molecular weight cut-off. The protein concentration and A330 absorbance of the 25 ml retentate and pooled permeate were determined. The ultrafiltered solution was subjected to diafiltration (DF) by a diavolume of 6, using 150 mL of solution with the same salt concentration and same pH as used for the extraction. At the end of the diafiltration both the retentate and pooled permeate from the diafiltration were analyzed for protein concentration and A330.

Aliquots of the final retentates were then passed through columns containing one of five different adsorbents and again protein concentration and A330 colour were tested on the resulting protein solutions. The adsorbents were Amberlite XAD-16 HP (polymeric absorbent), Amberlite SF120NA (a cation exchanger), Polyclar Super R (polyvinyl pyrrolidone), Silica gel (28 to 200 mesh), and granulated activated carbon (food grade).

The data obtained from the extraction experiments indicates that an extraction time of 30 minutes is sufficient to remove all extractive proteins from the meal. Beyond 30 minutes, no significant increase in extracted protein is seen at any of the pH or saline levels tested. The following Table I shows the amounts of extracted protein obtained at each pH and salt level:

TABLE I

Extracted Protein (g/L) at each pH and Salt Level at 60 minutes

|  | 0.0 M | 0.05 M | 0.10 M | 0.15 M | 0.25 M |
|---|---|---|---|---|---|
| pH 6.3 | 5.63 | 8.00 | 8.20 | 9.16 | 7.4 |
| pH 8.0 | 4.97 | 6.66 | 9.50 | 9.29 | 8.7 |
| pH 9.8 | 7.90 | 10.68 | 10.77 | 10.9 | 10.7 |
| pH 11.0 | 12.0 | 12.56 | 12.91 | 12.36 | 12.93 |

The following Tables II to VI show the effect of salt concentration on extracted protein (amounts in g/L) as a function of time at various pH levels:

TABLE II

| Saline Used: 0.0 M | pH 6.3 | pH 8.0 | pH 9.8 | pH 11.0 |
|---|---|---|---|---|
| T10 | 3.75 | 3.94 | 6.6 | 8.4 |
| T20 | 4.44 | 4.69 | 6.3 | 9.9 |
| T30 | 4.39 | 4.01 | 8.1 | 12.6 |
| T40 | 5.11 | 5.67 | 8.2 | 10.7 |
| T50 | 4.95 | 5.55 | 8.1 | 11.7 |
| T60 | 5.63 | 4.97 | 7.9 | 12 |

TABLE III

| Saline Used: 0.05 M | pH 6.3 | pH 8.0 | pH 9.8 | pH 11.0 |
|---|---|---|---|---|
| T10 | 7.3 | 5.87 | 8 | 10.5 |
| T20 | 8.3 | 8.11 | 9.5 | 12.04 |
| T30 | 7.4 | 6.6 | 9.6 | 12.7 |
| T40 | 7.5 | 7.3 | 10 | 12 |
| T50 | 7.9 | 7.3 | 10.7 | 13 |
| T60 | 8 | 6.7 | 10.7 | 12.6 |

TABLE IV

| Saline Used: 0.10 M | pH 6.3 | pH 8.0 | pH 9.8 | pH 11.0 |
|---|---|---|---|---|
| T10 | 9.2 | 9.7 | 8.4 | 14.4 |
| T20 | 8.4 | 9.6 | 10.13 | 13.17 |
| T30 | 9.2 | 9 | 11.25 | 12.4 |
| T40 | 9.3 | 8.9 | 11.23 | 12.57 |
| T50 | 8.9 | 9.5 | 11.83 | 13.18 |
| T60 | 8.2 | 9.5 | 10.77 | 12.91 |

TABLE V

| Saline Used: 0.15 M | pH 6.3 | pH 8.0 | pH 9.8 | pH 11.0 |
|---|---|---|---|---|
| T10 | 8.71 | 7.05 | 11.65 | 9.05 |
| T20 | 9.47 | 8.42 | 11.46 | 10.28 |
| T30 | 9.36 | 8.27 | 10.93 | 11.31 |
| T40 | 9.74 | 9.08 | 10.36 | 11.19 |
| T50 | 10.24 | 8.36 | 10.72 | 11.54 |
| T60 | 9.16 | 9.29 | 10.7 | 12.36 |

TABLE VI

| Saline Used: 0.25 M | pH 6.3 | pH 8.0 | pH 9.8 | pH 11.0 |
|---|---|---|---|---|
| T10 | 7.2 | 7.9 | 11.65 | 11.18 |
| T20 | 7.1 | 7.8 | 11.46 | 11.42 |
| T30 | 7.5 | 8.3 | 10.93 | 12.44 |
| T40 | 7.4 | 8.7 | 10.36 | 11.87 |
| T50 | 7.3 | 8.2 | 10.72 | 12.58 |
| T60 | 7.4 | 8.7 | 10.7 | 12.93 |

As may be seen from these Tables, higher pH extractions yielded higher protein contents at each salt level while increasing salt content beyond 0.05 M did not increase protein solubility, in the experiments performed.

The following Table VII shows the absorbance at 330 nm of the protein extract at each pH and salt level:

TABLE VII

The Effects of pH on A330 at Five Different Saline Concentrations

|  | 0.0 M | 0.05 M | 0.10 M | 0.15 M | 0.25 M |
|---|---|---|---|---|---|
| pH 6.3 | 21.2 | 23.6 | 58.5 | 48.8 | 51.6 |
| pH 8.0 | 27.2 | 42.1 | 66.8 | 52 | 52.5 |
| pH 9.8 | 32.8 | 39.7 | 36.2 | 31.9 | 27.9 |
| pH 11.0 | 43.1 | 42.1 | 42.8 | 36.9 | 42.9 |

As may be seen from Table VII, a reduction in extracted A330 colour occurs at pH 9.8 in extractions of 0.1 M, 0.15 M and 0.25 M. At this pH, the colour looks visibly darker than at other pH values and there is no corresponding drop in protein content. As noted above, the protein content of these extractions continues to rise through pH 9.8 and pH 11.0.

The following Table VIII shows the absorbance at 330 nm of the protein solution following ultrafiltration and prior to diafiltration while Table IX shows the A330 of the protein solution after diafiltration. As may be seen from these Tables, in each run, the A330 of the retentate was lower after having been diafiltered.

TABLE VIII

Retentate A330 prior to Diafiltration

|  | 0.0 M | 0.05 M | 0.10 M | 0.15 M | 0.25 M |
|---|---|---|---|---|---|
| pH 6.3 | 41.7 | 49.3 | 71.4 | 63.5 | 67.6 |
| pH 8.0 | 59.8 | 52 | 77.4 | 63.4 | 66.2 |
| pH 9.8 | 39.9 | 61.6 | 59.1 | 45 | 38.5 |
| pH 11.0 | 50.9 | 70.4 | 56.4 | 55.4 | 60.1 |

TABLE IX

Retentate A330 following Diafiltration

|  | 0.0 M | 0.05 M | 0.10 M | 0.15 M | 0.25 M |
|---|---|---|---|---|---|
| pH 6.3 | 29.8 | 18.0 | 15.0 | 22.2 | 17.6 |
| pH 8.0 | 37.9 | 22.7 | 36.1 | 22.5 | 22.1 |
| pH 9.8 | 15.2 | 38.8 | 25.1 | 34.4 | 19.9 |
| pH 11.0 | 34.8 | 35.1 | 34.4 | 31 | 40.1 |

The following Table X shows the percentage reduction in A330 achieved using diafiltration.

TABLE X

% Reduction in A330 by Diafiltration

|  | 0.0 M | 0.05 M | 0.10 M | 0.15 M | 0.25 M |
|---|---|---|---|---|---|
| pH 6.3 | 28.5 | 63.5 | 79.0 | 65.0 | 74.0 |
| pH 8.0 | 36.6 | 56.3 | 53.4 | 64.5 | 66.6 |
| pH 9.8 | 61.9 | 37 | 57.5 | 45.8 | 48.3 |
| pH 11.0 | 31.6 | 50.1 | 39.5 | 44.0 | 33.3 |

As may be seen from Table X, the greatest reduction in A330 value achieved following UF/DF came from 0.1 M extractions at pH 6.3. Of the five different saline levels tested, the lowest A330 value for all but one was achieved by extraction at pH 6.3.

The following Table XI shows the A330/g/L protein ratio to take into account different protein concentrations of final retentates. With this ratio, a low A330 and a high protein content indicated by a low resulting member is most desirable.

TABLE XI

A330/g/L for Retentates Following Diafiltration

|  | 0.0 M | 0.05 M | 0.10 M | 0.15 M | 0.25 M |
|---|---|---|---|---|---|
| pH 6.3 | 4.79 | 0.76 | 0.60 | 0.69 | 0.59 |
| pH 8.0 | 4.99 | 0.82 | 1.06 | 0.80 | 0.54 |
| pH 9.8 | 1.31 | 1.48 | 1.10 | 0.61 | n.a. |
| pH 11.0 | 0.69 | 0.80 | 0.96 | 0.83 | 0.67 |

As may be seen from Table XI, when the A330 to protein ratio is taken into account, the best results came from the 0.25 M saline series for each pH level tested, with the overall lowest A330/protein ratio coming from the 0.25 M extraction at pH 8.0, in the experiments performed.

Examination of the permeate A330 data (not shown) from both the ultrafiltration and the diafiltration suggests that more A330 is flushed out through the permeate at the two lower pH levels than at pH 9.8 and 11.0.

In testing the adsorbents, at pHs of 6.3 and 8.0, Polyclar reduced the free phenolics (A330) of the retentates and did not show a loss in protein following the adsorption step.

However, Polyclar at pH 9.8 and 11.0 did not recover significant amounts of free phenolics. Amberlite XAD reduced A330 in most cases, run at high pH, but protein also was lost, in about every case.

Of the other adsorbents tested, silica gel failed to reduce the A330 in most cases and quite often made the sample cloudy, leading to a higher A330 reading. Amberlite SF120 showed some reduction in A330 at lower pH levels but again did not appear to be as effective at the higher pH levels and in many cases showed a significant loss in protein. These samples also had some precipitation after passing through the adsorbent.

The granulated activated carbon (GAC) worked quite well at reducing A330 in the retentates at lower pH levels but did not effectively reduce A330 at pH 9.8 and 11.0. The GAC also exhibited some protein loss for most of the tests. The samples that had been passed through the GAC had to be filtered with a 0.45 µM filter following treatment owing to the presence of residual carbons.

Example 2

This Example illustrates the effect of addition of an anti-oxidant on the extraction step.

The procedure of Example 1 was repeated in which extractions were performed at pH 8.0 and pH 6.3 in 0.1 M saline with the addition of ascorbic acid and with purging of extraction medium with helium to remove 99% of the dissolved oxygen. A420 absorption was also determined as a measure of visible colour.

The following Table XII shows the extraction data:

TABLE XII

Extraction Data:

|  | Extracted Protein g/L | Extracted A330 | Extracted A420 |
| --- | --- | --- | --- |
| 0.1 M, pH 8.0 | 11.07 | 38.3 | 11.29 |
| 0.1 M, pH 8.0, 0.01% ascorbic | 11.34 | 47.5 | 5.41 |
| 0.1 M, pH 8.0, 0.05% ascorbic | 12.18 | 47.2 | 4.96 |

As may be seen from Table XII, the use of ascorbic acid in the extraction reduces visible colour as shown by A420. Low levels of ascorbic acid (0.05%) can result in greater than a two-fold reduction in extraction A420, or visible colour.

The following Table XIII shows the diafiltration retentate A330 and A420 readings:

TABLE XIII

Retentate A330 and A420 Readings

|  | UF Retentate A330 | DF Retentate A330 | DF Retentate A420 | DF Retentate g/L Protein | Retentate A330/ Protein Ratio |
| --- | --- | --- | --- | --- | --- |
| 0.1 M, pH 8.0 | 44.1 | 14.8 | 4.3 | 27.6 | 0.54 |
| 0.1 M, pH 8.0, 0.01% ascorbic | 58.2 | 16.5 | 3.29 | 30.6 | 0.54 |
| 0.1 M, pH 8.0, 0.05% ascorbic | 60.4 | 18.8 | 3.41 | 37.4 | 0.50 |

As may be seen from Table XIII, the reduction in A420 by ascorbic acid in the extraction is still reflected after diafiltration. The A420 of retentates from extractions with ascorbic acid were lower than retentates that did not have ascorbic acid in the extraction.

Table XIV shows the effect of Polyclar on A330 and A420 in retentates:

TABLE XIV

|  | A330 Before Treatment | A330 After Treatment | % A330 Reduction | A420 Before Treatment | A420 After Treatment | % A420 Reduction |
| --- | --- | --- | --- | --- | --- | --- |
| 0.1 M, pH 8.0 | 14.8 | 11.9 | 19.6 | 4.3 | 3.25 | 24.5 |
| 0.1 M, pH 8.0, 0.01% ascorbic | 16.5 | 10.1 | 38.8 | 3.29 | 2.41 | 26.8 |
| 0.1 M, pH 8.0, 0.05% ascorbic | 18.8 | 13.5 | 28.2 | 3.41 | 2.78 | 18.5 |

As may be seen from Table XIV, reduced A420 by ascorbic acid used in the extraction is still present even after treatment with an adsorbent. Polyclar reduced the A420 of each sample, but the two samples containing ascorbic acid were lower than the control without ascorbic acid.

Example 3

This Example also illustrates the effect of salt concentration and pH on the extraction with an anti-oxidant.

This Example is a repeat of Example 1, except that 0.5 g (0.1%) of sodium sulfite ($Na_2SO_3$) was added to the canola oil seed meal extraction liquid prior to commencement of the extraction step. All other parameters used were the same as in Example 1, except that the diavolume value was 5.

The following Tables XV.1 to XV.5 show the amounts of protein obtained at each pH and salt level:

TABLE XV.1

Extraction rate of runs with 0.0 M NaCl and 0.1% $Na_2SO_3$ (g/L)

| Time (min) | pH 6.3 | pH 8.0 | pH 9.8 | pH 11.0 |
| --- | --- | --- | --- | --- |
| 10 | 4.5 | 11.0 | 11.4 | 12.2 |
| 20 | 5.6 | 6.1 | 8.8 | 14.3 |
| 30 | 6.2 | 6.0 | 10.0 | 14.2 |
| 40 | 6.6 | 6.1 | 11.0 | 14.1 |
| 50 | 7.8 | 6.4 | 10.9 | 14.5 |
| 60 | 6.2 | 6.8 | 11.1 | 13.7 |

TABLE XV.2

Extraction rate of runs with 0.05 M NaCl and 0.1% $Na_2SO_3$ (g/L)

| Time (min) | pH 6.3 | pH 8.0 | pH 9.8 | pH 11.0 |
| --- | --- | --- | --- | --- |
| 10 | 9.2 | 8.9 | 8.9 | 11.1 |
| 20 | 8.7 | 8.7 | 9.9 | 11.1 |
| 30 | 9.2 | 8.5 | 9.0 | 12.2 |
| 40 | 9.1 | 8.4 | 10.6 | 12.4 |
| 50 | 9.5 | 8.5 | 10.0 | 13.0 |
| 60 | 10.5 | 7.3 | 10.9 | 13.8 |

TABLE XV.3

Extraction rate of runs with 0.10 M NaCl and 0.1% Na$_2$SO$_3$ (g/L)

| Time (min) | pH 6.3 | pH 8.0 | pH 9.8 | pH 11.0 |
|---|---|---|---|---|
| 10 | 8.4 | 8.3 | 9.2 | 11.3 |
| 20 | 9.7 | 9.1 | 10.3 | 11.5 |
| 30 | 10.1 | 9.0 | 10.3 | 11.3 |
| 40 | 9.2 | 9.0 | 9.8 | 11.4 |
| 50 | 10.4 | 9.4 | 10.0 | 12.3 |
| 60 | 10.1 | 9.1 | 10.8 | 11.3 |

TABLE XV.4

Extraction rate of runs with 0.15 M NaCl and 0.1% Na$_2$SO$_3$ (g/L)

| Time (min) | pH 6.3 | pH 8.0 | pH 9.8 | pH 11.0 |
|---|---|---|---|---|
| 10 | 8.8 | 11.0 | 11.2 | 13.0 |
| 20 | 9.5 | 10.6 | 12.5 | 13.7 |
| 30 | 8.3 | 11.4 | 12.6 | 14.0 |
| 40 | 8.8 | 10.8 | 12.4 | 14.4 |
| 50 | 9.6 | 10.5 | 12.7 | 13.6 |
| 60 | 9.8 | 10.6 | 12.5 | 14.1 |

TABLE XV.5

Extraction rate of runs with 0.25 M NaCl and 0.1% Na$_2$SO$_3$ (g/L)

| Time (min) | pH 6.3 | pH 8.0 | pH 9.8 | pH 11.0 |
|---|---|---|---|---|
| 10 | 11.5 | 10.7 | 12.7 | 12.3 |
| 20 | 11.0 | 12.8 | 14.0 | 13.0 |
| 30 | 12.1 | 13.4 | 14.8 | 13.4 |
| 40 | 11.8 | 18.4 | 14.6 | 13.1 |
| 50 | 12.3 | 12.4 | 14.7 | 14.1 |
| 60 | 12.2 | 13.4 | 15.2 | 14.4 |

As may be seen from these Tables, extraction reached equilibrium in about 30 minutes in most runs. When no salt was added, more protein was extracted as the pH was raised. The effect of pH seemed less significant at pH below 8.0 than at high pH above 9.8 (Table XV.1). Salt addition at low levels (less than 0.10 M) was able to substantially increase the protein extractability at pH 6.3 and 8.0, but low salt concentrates did not assist protein extraction at higher pH levels of 9.8 or 11.0 (Tables XV.2 and XV.3).

The following Tables XVI shows the effect of pH and sodium chloride concentration on the free phenolic content (A330 absorbance) of the protein extract:

TABLE XVI

Effect of pH and NaCl concentration on A330 of protein extract (with Na$_2$SO$_3$)

| | 0 NaCl | 0.05 M NaCl | 0.10 M NaCl | 0.15 M NaCl | 0.25 M NaCl |
|---|---|---|---|---|---|
| pH 6.3 | 41.1 | 49.1 | 34.5 | 51.1 | 54.2 |
| pH 8.0 | 24.3 | 36 | 38.3 | 39.9 | 41.8 |
| pH 9.8 | 30 | 28.2 | 27.5 | 27.8 | 29 |
| pH 11.0 | 38.4 | 29.7 | 32.7 | 31.5 | 32.1 |

As seen in this Table XVII, the A330 showed a decreasing value with rising pH to pH 9.8 although the protein concentration also increased over this range. The colour extract became visibly darker as the pH rose. The salt concentration had a less pronounced effect on colour.

The following Tables XVII.1 to XVII.4 show the effect of pH and NaCl concentration on A330 of retentate (Table XVII.1) and permeate (Table XVII.2) from ultrafiltration and on A330 of retentate (Table XVII.3) and permeate (Table XVII.4) from diafiltration.

TABLE XVII.1

Effect of pH and NaCl concentration on A330 of retentate from ultrafiltration (with Na$_2$SO$_3$)

| | 0 NaCl | 0.05 M NaCl | 0.10 M NaCl | 0.15 M NaCl | 0.25 M NaCl |
|---|---|---|---|---|---|
| pH 6.3 | 88.7 | 71.9 | 44.4 | 73.2 | 75.3 |
| pH 8.0 | 18.3 | 55.2 | 60.0 | 62.3 | 65.5 |
| pH 9.8 | 55.9 | 48.1 | 59.1 | 49.7 | 54.2 |
| pH 11.0 | 77.6 | 57.4 | 56.4 | 61.8 | 62.3 |

TABLE XVII.2

Effect of pH and NaCl concentration on A330 of permeate from ultrafiltration (with Na$_2$SO$_3$)

| | 0 NaCl | 0.05 M NaCl | 0.10 M NaCl | 0.15 M NaCl | 0.25 M NaCl |
|---|---|---|---|---|---|
| pH 6.3 | 31.3 | 40.6 | 24.8 | 43.4 | 41.8 |
| pH 8.0 | 16.0 | 35.9 | 29.8 | 34.4 | 30.1 |
| pH 9.8 | 25.2 | 20.6 | 23.5 | 23.9 | 24.0 |
| pH 11.0 | 25.1 | 21.3 | 23.3 | 25.4 | 25.1 |

TABLE XVII.3

Effect of pH and NaCl concentration on A330 of retentate from diafiltration (with Na$_2$SO$_3$)

| | 0 NaCl | 0.05 M NaCl | 0.10 M NaCl | 0.15 M NaCl | 0.25 M NaCl |
|---|---|---|---|---|---|
| pH 6.3 | 34.8 | 24.7 | 14.9 | 21.2 | 21.2 |
| pH 8.0 | 13.9 | 17.8 | 20.8 | 20.0 | 23.7 |
| pH 9.8 | 30.6 | 34.3 | 32.3 | 20.2 | 22.1 |
| pH 11.0 | 58.5 | 29.0 | 24.8 | 35.0 | 24.5 |

TABLE XVII.4

Effect of pH and NaCl concentration on A330 of permeate from diafiltration (with Na$_2$SO$_3$)

| | 0 NaCl | 0.05 M NaCl | 0.10 M NaCl | 0.15 M NaCl | 0.25 M NaCl |
|---|---|---|---|---|---|
| pH 6.3 | 7.0 | 8.5 | 6.3 | 7.9 | 8.5 |
| pH 8.0 | 3.1 | 10.0 | 6.0 | 6.5 | 5.7 |
| pH 9.8 | 8.3 | 8.0 | 6.9 | 7.0 | 5.7 |
| pH 11.0 | 6.8 | 5.4 | 5.1 | 5.8 | 5.2 |

Since ultrafiltration concentrated the protein in the extract four times, the retentate was visibly much darker and had a higher A330 reading than the extract (Table XVII.1) except for 0.0 NaCl at pH 8.0, but the latter may be an anomalous result. Similar to the original extract before UF, a minimum in A330 occurred at pH 9.8, which was not supported by the actual visible colour darkness for reasons previously discussed. Measured at A330, UF recovered a substantial amount of the phenolics from the extract as shown by the high A330 reading in the permeate (see Table XVII.2).

From Table XVII.3, it can be seen that diafiltration retentate had a much lower A330 reading than the UF retentate (Table XVII.1). Although the DF permeate (Table XVII.4)

was not as high in A330 reading as that of UF permeate (Table XVII.4), the DF nevertheless resulted in the further removal of considerable amounts of the remaining phenolics. This additional removal of phenolics by diafiltration resulted in a much lower A330 in the DF retentate (Table XVII.3) than in the UF retentate (Table VII.1).

The following Table XVIII.1 to XVIII.4 show the effect of adsorbents and pH on A330 of retentate:

TABLE XVIII.1

Effect of adsorbents and pH on A330 of retentate (0.05 M NaCl with 0.1% $Na_2SO_3$)

| pH | Control | Polyclar | XAD | SF 120 | Silica gel |
|---|---|---|---|---|---|
| 6.3 | 24.7 | 14.8 | 21.7 | 19.5 | 20.8 |
| 8.0 | 17.8 | 13.8 | 15.8 | 18.8 | 19.9 |
| 9.8 | 34.3 | 30.8 | 32.4 | 38.6 | 41.2 |
| 11.0 | 29 | 28.7 | 25.1 | 29.8 | 30.5 |

TABLE XVIII.2

Effect of adsorbents and pH on A330 of retentate (0.10 M NaCl with 0.1% $Na_2SO_3$)

| pH | Control | Polyclar | XAD | SF 120 | Silica gel | GAC |
|---|---|---|---|---|---|---|
| 6.3 | 14.9 | 10.9 | 9.5 | 14.6 | 12.6 | 11.8 |
| 8.0 | 20.8 | 15.8 | 16.6 | 19.9 | 22.7 | 19.1 |
| 9.8 | 32.3 | 22.7 | 32 | 31.1 | 36.2 | 26.4 |
| 11.0 | 24.8 | 23.3 | 23.2 | 26.5 | 28.2 | 26.6 |

TABLE XVIII.3

Effect of adsorbents and pH on A330 of retentate (0.15 M NaCl with 0.1% $Na_2SO_3$)

| pH | Control | Polyclar | XAD | SF 120 | Silica gel | GAC |
|---|---|---|---|---|---|---|
| 6.3 | 21.2 | 13.5 | 15.7 | 18.3 | 18.7 | 19.4 |
| 8.0 | 20 | 16 | 16.3 | 17.9 | 19.5 | 19.5 |
| 9.8 | 20.2 | 18 | 16.1 | 21 | 29.8 | 20 |
| 11.0 | 35 | 28 | 31.6 | 33.6 | 35.2 | 34.2 |

TABLE XVIII.4

Effect of adsorbents and pH on A330 of retentate (0.25 M NaCl with 0.1% $Na_2SO_3$)

| pH | Control | Polyclar | XAD | SF 120 | Silica gel | GAC |
|---|---|---|---|---|---|---|
| 6.3 | 21.2 | 15.9 | 16.6 | 21.4 | 20.4 | 21.4 |
| 8.0 | 23.7 | 16.1 | 21 | 24.5 | 25.7 | 24.5 |
| 9.8 | 22.1 | 19.1 | 21.1 | 22.9 | 26.5 | 22.7 |
| 11.0 | 24.5 | 22.8 | 18.4 | 24.2 | 27.5 | 25.1 |

As may be seen from Tables XVIII.1 to XVIII.4, at low pH (<9.8), Polyclar, among all adsorbents tested, was particularly effective in decreasing the A330 reading in the final retentate. As seen in Table XVIII.1, the A330 value may be reduced by up to 40%.

Although other adsorbents were also able to lower A330 readings under specific conditions of pH and salt concentration, their effect was somewhat insignificant when compared to that of Polyclar. When pH of 9.8 was used, Polyclar was less useful in lowering A330.

The following Tables XVIII.5 to XVIII.8 show the effect of absorbents on protein concentration (g/L) in the retentate:

TABLE XVIII.5

Effect of adsorbents and pH on protein concentration of retentate (0.05 M with 0.1% $Na_2SO_3$)

| pH | Control | Polyclar | XAD | SF 120 | Silica gel |
|---|---|---|---|---|---|
| 6.3 | 51.5 | 53.2 | 47.1 | 46.3 | 46.5 |
| 8.0 | 39 | 46 | 37.2 | 48.5 | 41.4 |
| 9.8 | 40.4 | 41.1 | 38.5 | 38.3 | 41.1 |
| 11.0 | 48.2 | 51.5 | 47.8 | 50.6 | 49.1 |

TABLE XVIII.6

Effect of adsorbents and pH on protein concentration of retentate (0.10 M with 0.1% $Na_2SO_3$)

| pH | Control | Polyclar | XAD | SF 120 | Silica gel | GAC |
|---|---|---|---|---|---|---|
| 6.3 | 43.6 | 46 | 41.4 | 43.9 | 45.7 | 44.3 |
| 8.0 | 50.5 | 55.1 | 51.7 | 50.3 | 52 | 52.8 |
| 9.8 | 42.5 | 47.3 | 43.9 | 44.2 | 45.4 | 46 |
| 11.0 | 38 | 42 | 36.3 | 38.2 | 39.4 | 39.8 |

TABLE XVIII.7

Effect of adsorbents and pH on protein concentration of retentate (0.15 M with 0.1% $Na_2SO_3$)

| pH | Control | Polyclar | XAD | SF 120 | Silica gel | GAC |
|---|---|---|---|---|---|---|
| 6.3 | 33.5 | 36.2 | 32.3 | 34.7 | 36.9 | 33.3 |
| 8.0 | 46.8 | 48.7 | 44.2 | 46.4 | 48.2 | 47.4 |
| 9.8 | 39.5 | 40.9 | 36.2 | 39.7 | 39.7 | 40.4 |
| 11.0 | 56.2 | 59.5 | 50.4 | 55.8 | 60.1 | 58.5 |

TABLE XVIII.8

Effect of adsorbents and pH on protein concentration of retentate (0.25 M with 0.1% $Na_2SO_3$)

| pH | Control | Polyclar | XAD | SF 120 | Silica gel | GAC |
|---|---|---|---|---|---|---|
| 6.3 | 38.8 | 41.7 | 36.2 | 38.4 | 40.7 | 39 |
| 8.0 | 44.7 | 46.4 | 41.4 | 43.5 | 45.8 | 45.8 |
| 9.8 | 50.3 | 54 | 48.8 | 50.5 | 52.2 | 51.7 |
| 11.0 | 41.9 | 47.2 | 38.6 | 41.4 | 44.6 | 42.5 |

As may be seen from Tables XIVIII.5 to XVIII.8, all adsorbents tested were quite inert to protein concentration in the retentate at all combinations of salt and pH, even though the protein was much concentrated by ultrafiltration.

Example 4

This Example describes the effect of using lower levels of sodium sulfite and of purged extraction.

The procedure of Example 3 was repeated employing a lower level of sodium sulfite (0.05 wt % $Na_2SO_3$) for three runs at pH 8.0 using Polyclar as the adsorbent. A420 was measured in addition to A330.

In another set of experiments, the extract solution containing 0.05 wt % $Na_2SO_3$ also was purged with helium before and during extraction.

The following Table XIX.1 shows the effect of these modifications on protein extraction:

TABLE XIX.1

| | Protein extraction at pH 8.0 (g/L) | | |
|---|---|---|---|
| | 0.1% $Na_2SO_3$ | 0.05% $Na_2SO_3$ | He purge |
| 0.05 M NaCl | 8.5 | 11.8 | 11.5 |
| 0.10 M NaCl | 9.0 | 12.7 | 12.0 |
| 0.15 M NaCl | 11.4 | 14.3 | 14.5 |

As may be seen from Table XIX.1, at all three salt addition levels, protein concentration in the extract increased by about 40 wt % when reduced quantities of sodium sulfite were used. The higher salt concentration led to a higher protein concentration. The helium purge had no bearing on protein extraction.

Table XIX.2 shows the effect of these modifications on colour at A330:

TABLE XIX.2

| | Absorbance of extract at 330 nm | | |
|---|---|---|---|
| | 0.1% $Na_2SO_3$ | 0.05% $Na_2SO_3$ | He purge |
| 0.05 M NaCl | 36.0 | 40.5 | 35.9 |
| 0.10 M NaCl | 38.3 | 36.6 | 42.3 |
| 0.15 M NaCl | 39.9 | 43.4 | 42.7 |

As may be seen from Table XIX.2, the reduction in $Na_2SO_3$ did not significantly affect the A330 of the extract. Although the helium purge removed 99% of the dissolved oxygen, the absorbance of the extract was not improved either at 330 nm or 420 nm (Table XIX.3 below):

TABLE XIX.3

| | Absorbance of extract at 420 nm | |
|---|---|---|
| | No purge | He purge |
| 0.05 M NaCl | 9.0 | 9.4 |
| 0.10 M NaCl | 8.8 | 7.1 |
| 0.15 M NaCl | 8.4 | 10.0 |

The following Table XX shows the effect of membrane processing on the A330 and A420 of retentate:

TABLE XX

| | Effect of membrane processing on the A330 and A420 of retentate | | | | | |
|---|---|---|---|---|---|---|
| | Extract | | UF retentate | | DF retentate | |
| Salt | A330 | A420 | A330 | A420 | A330 | A420 |
| 0.05 M | 40.5 | 9.0 | 57.9 | 10.9 | 20.7 | 4.1 |
| 0.10 M | 36.6 | 8.8 | 55.9 | 10.9 | 15.1 | 3.5 |
| 0.15 M | 43.4 | 8.4 | 69.9 | 11.4 | 20.2 | 5.4 |
| 0.05 M w He* | 35.9 | 9.4 | 55.3 | 12.4 | 18.3 | 4.0 |
| 0.10 M w He | 42.3 | 7.1 | 67.0 | 10.4 | 20.5 | 4.7 |
| 0.15 M w He | 42.7 | 10.0 | 61.3 | 12.9 | 20.2 | 4.3 |

*with helium purge

As seen in Table XX, diafiltration substantially removed the coloured components in the extract. Both A330 and A420 readings for the final retentate were about half those of the original extract. Helium purge had no effect on A330 or A420 values.

The following Table XXI shows the effect of Polyclar on A330 and A420 of retentate:

TABLE XXI

| | Effect of Polyclar on A330 and A420 | | | |
|---|---|---|---|---|
| | Control | | Polyclar* | |
| Salt | A330* | A420* | A330 | A420 |
| 0.05 M | 20.7 | 4.1 | 14.9 (28%) | 3.6 (12%) |
| 0.10 M | 15.1 | 3.5 | 11.3 (25%) | 2.7 (23%) |
| 0.15 M | 20.2 | 5.4 | 16.1 (20%) | 4.6 (15%) |
| 0.05 M w He** | 18.3 | 4.0 | 12.5 (32%) | 3.6 (10%) |
| 0.10 M w He | 20.5 | 4.7 | 18.5 (10%) | 4.1 (13%) |
| 0.15 M w He | 20.2 | 4.3 | 13.9 (31%) | 3.8 (12%) |

*Numbers in brackets are the percentages of reduction
**with helium purge

Example 5

This Example illustrates the preparation of a canola protein isolate from commercial canola meal using an antioxidant and diafiltration.

150 kg of commercial canola meal (higher temperature toasted meal) was added to 1000 L of 0.15 M NaCl containing 0.5 kg (0.05 wt %) ascorbic acid solution at 16° C. and agitated for 30 minutes to provide an aqueous protein solution having a protein content of 20.2 g/L. The residual canola meal was removed and washed on a vacuum filter belt. The resulting protein solution was clarified by centrifugation and filtration to produce 1040 L of a clarified protein solution having a protein content of 14.6 g/L.

The protein extract solution was reduced in volume to 45 L by concentration on an ultrafiltration system using 5000 dalton molecular weight cut-off membranes. The protein extract solution then was diafiltered on a diafiltration system using 5000 dalton molecular weight cut-off membranes with 450 L of 0.15 M NaCl solution containing 0.05 wt % ascorbic acid to a final volume of 44 L with a protein content of 225 g/L.

The concentrated and diafiltered solution at 30° C. was diluted 1:15 into 4° C. water. A white cloud of protein micelles formed immediately and was allowed to settle. The upper diluting water was removed and the precipitated, viscous, sticky mass (PMM) was recovered from the bottom of the vessel and dried. The dried protein was found to have a protein content of 103.2 wt % (N×6.25) d.b.

620 L of supernatant from the micelle formation were concentrated to 30 L by concentration on an ultrafiltration system using 5000 dalton molecular weight cut-off membranes. The concentrated supernatant then was diafiltered on a diafiltration system using 5000 dalton molecular weight cut-off membranes with 100 L of water to a final volume of 27 L with a protein content of 121.8 g/L.

The concentrated and diafiltered solution was dried. The dried protein was found to have a protein content of 100.8 wt % (N×6.25) d.b.

Samples of the PMM-derived canola protein isolate (CPI) and the supernatant-derived canola protein isolate were evaluated for lightness (L) and chromaticity (a and b) using a Minolta (CR-310) colorimeter. In the Lab space, the value moves from 0 to 100, with 100 being white and 0 being black. The chromaticity coordinates, a and b, both have maximum values of +60 and −60, +a being the red direction, −a being the green direction, +b being the yellow direction and −b being the blue direction.

The following Table XXII shows the results obtained:

TABLE XXII

| Sample | L | a | b |
|---|---|---|---|
| PMM-derived CPI | 83.08 | −1.58 | +27.89 |
| Supernatant-derived CPI | 79.38 | −0.11 | +20.46 |

The canola protein isolates exhibited a lighter (L) and less yellow (b) colour than isolates produced following this procedure but omitting the addition of ascorbic acid (as an antioxidant) and the diafiltration steps (data not shown).

Example 6

This Example illustrates the effect of temperature on the colour of protein extracts from a low temperature toasted meal and an air-desolventized meal.

75 g samples of a (a) low-temperature toasted (100° C.) canola oil seed meal (LT) and (b) an air-desolventized (20° C.) canola oil seed meal (Marc) were added to 500 samples of 0.15 M NaCl solution at ambient or room temperature (RT), 55° C., 60° C. and 65° C., agitated for 30 minutes while maintaining the temperature of the solution substantially constant to provide aqueous protein solutions. Samples of the aqueous protein solution were taken at 5, 10, 15, 20 and 30 minutes for analysis. The spent meal was separated by centrifugation at 10,000×g for 5 minutes and freeze dried.

Absorbances at A330 and A420 were determined for the various protein solution samples. As already noted above UV absorbance at A330 is indicative of phenolics concentration in solution while absorbance at A420 is more direct measurement of actual colour. The data for the various samples are set forth in the following Tables XXIII AND XXIV:

TABLE XXIII

Absorbance Readings for Extracts of Low-temperature Meal

| Extraction | RT | | 55° C. | | 60° C. | | 65° C. | |
|---|---|---|---|---|---|---|---|---|
| Time (min) | A330 | A420 | A330 | A420 | A330 | A420 | A330 | A420 |
| 5 | 80.7 | 1.96 | 97.2 | 2.70 | 99.8 | 3.03 | 98.3 | 2.84 |
| 10 | 88.9 | 2.42 | 92.0 | 2.77 | 98.0 | 3.07 | 93.9 | 2.95 |
| 15 | 92.5 | 2.50 | 89.1 | 2.94 | 95.6 | 3.10 | 93.0 | 3.05 |
| 20 | 90.7 | 2.55 | 86.1 | 2.90 | 93.7 | 3.23 | 90.7 | 3.16 |
| 30 | 90.7 | 2.56 | 88.2 | 3.22 | 97.8 | 3.47 | 88.1 | 3.24 |

TABLE XXIV

Absorbance Readings for Extracts of Marc Meal

| Extraction | RT | | 55° C. | | 60° C. | | 65° C. | |
|---|---|---|---|---|---|---|---|---|
| Time (min) | A330 | A420 | A330 | A420 | A330 | A420 | A330 | A420 |
| 5 | 120.3 | 2.73 | 118.8 | 2.94 | 120.5 | 3.08 | 128.4 | 3.16 |
| 10 | 116.7 | 2.73 | 118.5 | 3.07 | 121.1 | 3.15 | 127.4 | 3.19 |
| 15 | 117.0 | 2.78 | 119.5 | 3.20 | 116.3 | 3.09 | 112.5 | 3.04 |
| 20 | 119.1 | 2.84 | 113.1 | 3.17 | 112.9 | 3.19 | 121.6 | 3.09 |
| 30 | 114.1 | 2.74 | 113.1 | 3.23 | 114.6 | 3.22 | 119.1 | 3.00 |

As may be seen from Tables XXIII and XXIV, elevating the extraction temperature had no significant effect on the A330 of the extracted protein solution for each meal type tested but there was a slight increase in the A420 readings seen at higher temperatures.

Example 7

This Example shows the effects of certain parameters on colour of protein extracts from certain canola oil seed meals.

In a first set of experiments, 50 g samples of canola oil seed meal which (a) had been low temperature toasted at 100° C. (LT meal) or (b) which had been air-desolventized at 20° C. (Marc meal) were added to 500 mL samples of 0.05 M or 0.10 M NaCl solution at room temperature (20° C.) and stirred for 15 minutes. The slurry was centrifuged at 5000×g for 10 minutes to remove spent meal.

In a second set of experiments, 500 mL of water with no salt added was first heated to 60° C. on a hot plate stirrer. Then 50 g of canola oil seed meal, which had been low temperature toasted at 100° C., or (b) which had been air-desolventized at 20° C. (Marc meal), was added and stirred for 15 minutes while the temperature was maintained. The extract was separated from the spent meal by centrifugation at 5000×g for 10 minutes.

Absorbances at A330 and A420 and protein concentrations were determined for the various protein solutions. The results obtained are set forth in the following Table XXV.1 and XXV.2:

TABLE XXV.1

Absorbance Readings for Extracts

| | 0.05 M saline | | 0.10 M saline | | 60° C. water | |
|---|---|---|---|---|---|---|
| | A330 | A420 | A330 | A420 | A330 | A420 |
| LT meal | 62.4 | 1.88 | 64.4 | 1.84 | 55.4 | 2.10 |
| Marc meal | 77.7 | 1.82 | 85.5 | 2.10 | 78.0 | 2.13 |

| | 0.05 M Saline | 0.1 M Saline | 60° C. Water |
|---|---|---|---|
| LT Meal | 1.11 | 1.44 | 0.98 |
| Marc Meal | 2.09 | 2.04 | 1.38 |

As may be seen from the results contained in Table XXV.1 and XXV.2, the A330 values increase with increasing protein concentration while colour intensity, as indicated by A420, did not change significantly with the protein concentration, coinciding with visual observation. These results show that, along with a higher protein yield, a lighter product may be expected from the air-desolventized meal in comparison with low temperature toasted meal.

Example 8

This Example shows the effect of solvent extraction of canola protein isolate on product colour.

A mixture of PMM-derived canola protein isolates was formed from three isolation procedures, such PMM-derived isolates being D29-02A C300 (57.9 wt %), D24-02A C300 (34.7 wt %) and D11-02A C300 (7.4 wt %) (Composite 6). In addition a mixture of supernatant-derived isolates was formed from three isolation procedures, such supernatant-derived isolates being E29-02A C200 (18.7 wt %), D29-02A C200 (40.1 wt %) and E14-02A C200 (41.2 wt %) (Composite 7).

The specific procedures utilized to prepare the individual canola protein isolates are as follows:

'a' kg of commercial canola meal was added to 'b' L of 0.15 M NaCl solution at ambient temperature, agitated for 30 minutes to provide an aqueous protein solution having a protein content of 'c' g/L. The residual canola meal was removed and washed on a vacuum filter belt. The resulting protein solution was clarified by centrifugation and filtration to produce 'd' L of a clarified protein solution having a protein content of 'e' g/L.

A 'f' L aliquot of the protein extract solution was reduced in volume to 'g' L by concentration on an ultrafiltration system using 'h' dalton molecular weight cutoff membranes. The resulting concentrated protein solution had a protein content of 'i' g/L.

The concentrated solution at 'j' ° C. was diluted 'k' into 4° C. water. A white cloud formed immediately and was allowed to settle. The upper diluting water was removed and the precipitated, viscous, sticky mass (PMM) was recovered from the bottom of the vessel in a yield of 'l' wt % of the extracted protein. The dried PMM derived protein was found to have a protein content of 'm' % (N×6.25) d.b. The product was given designation 'n'.

The following Table XXVI gives the values of the parameters 'a' to 'm':

TABLE XXVI

| n | BW-AL017-D11-02A C300 | BW-AL017-D24-02A C300 | BW-AL017-D29-02A C300 | BW-AL017-E14-02A C300 | BW-AL018-E29-02A C300 |
|---|---|---|---|---|---|
| a | 1200 | 150 | 150 | 150 | 150 |
| b | 8000 | 1000 | 1000 | 999 | 1001 |
| c | 26.3 | 25.7 | 20.2 | 20 | 24.4 |
| d | 5882 | 1152 | 1040 | 1245 | 1075 |
| e | 17.7 | 16.6 | 14.6 | 10.2 | 17.8 |
| f | 5882 | 1080 | 1040 | 1194 | 820 |
| g | 92 | 53 | 44.25 | 39 | 24 |
| h | 5000 | 5000 | 5000 | 5000 | 5000 |
| i | 289 | 246.8 | 225 | 238 | 289 |
| j | 31 | 32 | 32 | 32 | 32 |
| k | 1:15 | 1:15 | 1:15 | 1:15 | 1:15 |
| l | 8.5 | 37.3 | 29.4 | 27.7 | 23.9 |
| m | 104.4 | 105.1 | 103.2 | 100.1 | 102.4 |

The removed diluting water was reduced in volume by ultrafiltration using a 'o' dalton molecular weight cut-off membrane to a protein concentration of 'p' g/L. The concentrate was dried. With the additional protein recovered from the supernatant, the overall protein recovery was 'q' wt % of the extracted protein. The dried protein formed had a protein content of 'r' wt % (N×6.25) d.b.

The product was given designation 's'. The following Table XXVII gives the values for the parameters 'o' to 'r':

TABLE XXVII

| s | BW-AL017-D11-02A C200 | BW-AL017-D24-02A C200 | BW-AL017-D29-02A C200 | BW-AL017-E14-02A C200 | BW-AL018-E29-02A C200 |
|---|---|---|---|---|---|
| o | 3000 | 5000 | 5000 | 5000 | 5000 |
| p | 237.6 | 194.4 | 121.8 | 115.8 | 100.1 |
| q | 15.5 | 55.4 | 45.7 | 44.4 | 35.2 |
| r | 98.7 | 97.8 | 100.8 | 98.7 | 97.5 |

1.4 kg of Composite 6 was dispersed in a blend of 3L of ethanol (denatured: 85% ethanol/15% wood alcohol, VWR Canlab D and 3L of reverse osmosis (RO) purified water. The mixture was stirred for 30 minutes using an overhead stirrer. Solid material was separated from the bulk liquid by centrifuging the sample in batches at 8000 g for 5 minutes.

The pellets were then redispersed and extracted again in a further blend of 3L of ethanol and 3L of RO water for 30 minutes with stirring. Centrifugation (8000 g/5 min.) again was used to collect the solid sample. The pellets were then dispersed into 4L of ethanol in an effort to remove water from the samples. The solid material was collected by centrifugation (8000 g/5 min.) and re-dispersed in 4L of fresh ethanol.

Centrifugation (8000 g/5 min.) again was used to collect the solids. The pellets were broken up and spread on a baking sheet and left in a fumehood to dry.

This procedure was repeated using 1.4 kg of Composite 7, which was dispersed in a blend of 4.2 L of ethanol and 1.8 L of reverse osmosis purified water. The pellets were redispersed in a fresh blend of 4.2L of ethanol and 1.8L of RO water.

The protein powders obtained and solvent extract samples were analyzed for total protein content and by HPLC. Protein powders were also analyzed for moisture content. Solvent extract samples were also examined using a spectrophotometer to give an indication of their phenolic content (absorbance at 330 nm) and visible colour (absorbance at 420 nm). The colour of the dry protein products was assessed using a Minolta CR-310 colour meter.

The recovery of ethanol/water-extracted Composite 6 was 86 wt % and for Composite 7 was 80 wt %. Product losses were due to solubility in the extraction solvent and the following Table XXVIII gives the protein content of the solvent extracts.

TABLE XXVIII

Protein content of solvent extracts

| Sample | wt % protein |
|---|---|
| Composite 6 - first extraction | 1.12 |
| Composite 6 - second extraction | 0.46 |
| Composite 7 - first extraction | 1.55 |
| Composite 7 - second extraction | 1.27 |

Other losses are attributable to material lost due to handling of the samples.

The colour readings obtained are set forth in the following Table XXIX:

TABLE XXIX

Colour readings for composite sample before and after extraction

| Sample | L | a | B |
|---|---|---|---|
| Composite 6 before extraction | 81.49 | +0.12 | +24.37 |
| Composite 6 after extraction | 83.53 | −0.56 | +14.18 |
| Composite 7 before extraction | 79.68 | +0.20 | +19.69 |
| Composite 7 after extraction | 80.67 | +0.13 | +14.72 |

As may be seen from the data in Table XXIX, for both Composite 6 and Composite 7, the extraction of the canola protein isolate resulted in an increase in lightness (L), a decrease in "a" value and a decrease in "b" value. The increase in L value means the product is more white and less black. The decrease in "a" value corresponds to a shift in colour from red towards green while the decrease in "b" value corresponds to a shift in colour from yellow towards blue. The reduction in redness and yellowness of the samples is an indication of the removal of phenolic compounds and/or their reaction products.

In the following Table XXX provides the absorbance readings for solvent extracts:

TABLE XXX

Absorbance readings for solvent extracts

| Sample | A420 | A330 |
|---|---|---|
| Composite 6 - first extract | 3.19 | 21.60 |
| Composite 6 - second extract | 0.82 | 6.00 |
| Composite 7 - first extract | 3.20 | 11.40 |
| Composite 7 - second extract | 0.80 | 3.00 |

As may be seen from Table XXX, the extracts are lightly coloured, indicating extraction of colourants from the protein isolate.

Table XXXI shows the protein content (N×6.25. Percentage nitrogen values were determined using a Leco FP52D Nitrogen Determinator) and moisture content of the solvent extracted protein isolates:

TABLE XXXI

Characteristics of solvent extracted protein isolates

| Sample | Protein content (wt % w.b.) | Moisture content (wt %) |
|---|---|---|
| Composite 6 | 97.35 | 6.13 |
| Composite 7 | 94.09 | 3.75 |

As may be seen from Table XXXI, the solvent extracted products were low in moisture and had a protein content sufficiently high for the products to be classified as isolates

Example 9

This Example illustrates the use of an antioxidant and adsorbent in the production of a canola protein isolate.

150 kg of a commercial canola oil seed meal which had been desolventized at low temperature (100° C.) was added to 1000L of 0.15 M NaCl and mixed for 30 minutes at a room temperature of 21° C. After 15 minutes of mixing 0.05 wt % (500 g) of ascorbic acid was added to the slurry as an antioxidant.

The residual canola meal was removed and washed on a vacuum filter belt resulting in 953.5 L of protein solution having a protein content of 23.9 g/L. The UV absorbance of the solution at 330 nm was 61.2.

21.2 kg (2.2 wt %) Polyclar Super R was added to the 953.5 L of protein solution and allowed to mix for 1 hour at room temperature. Thereafter, the Polyclar was removed by passing the protein solution through a desludger centrifuge and then filter presses containing 20 and 0.2 µM filter pads, respectively. Following Polyclar removal, 842 L of canola protein solution was collected having a protein content of 19.9 g/L and a A330 absorbance of 33.2. A significant drop in the A330 absorbance, therefore, was obtained, with a very low protein loss.

The clarified solution then was concentrated to a volume of 30 L having a protein content of 338.4 g/L and an A330 of 20.4 on an ultrafiltration system using 5000 dalton molecular weight cut-off membranes. The concentrated protein extract solution was diafiltered on a diafiltration system using 5000 dalton molecular weight cut-off membranes with 300 L of 0.15M NaCl containing 0.05 wt % ascorbic acid. The resulting 29.0 L of concentrated and diafiltered canola protein solution had a protein content of 299.7 g/L and an A330 of 25.6.

In contrast to the results seen in Examples 1 to 3 and 5, the diafiltration had little effect on A330, likely because the Polyclar had already removed much of the free phenolic, from the canola protein solution prior to the concentration step.

The concentrated and diafiltered solution at 31° C. was diluted into 15 volumes of water having a temperature of 6.4° C. A white cloud of protein micelles formed immediately and was allowed to settle for two hours. The upper diluting water was removed and the precipitated, viscous, sticky mass (PMM) (40.6 kg) was recovered from the bottom of the vessel and spray dried. The dried protein isolate had a protein content of 98.8 wt % (N×6.25) d.b.

440 L of supernatant from the micelle formation and having a protein content of 13.3 g/L were concentrated to 30 L by concentration on an ultrafiltration system using 5,000 dalton molecular weight cut-off membranes. The concentrated supernatant then was diafiltered on a diafiltration system using 5,000 dalton molecular weight cut-off membranes with five volumes of water. The resulting solution had a protein content of 161.0 g/L and an A330 of 10.8.

The concentrated and diafiltered solution was dried and the dried protein was found to have a protein content of 95.6 wt % (N×6.25) d.b.

Samples of the PMM-derived canola protein isolate (CPI) and the supernatant-derived canola protein isolate were analyzed for lightness (L) and chromaticity (a and b) using a Minolta CR-310 calorimeter.

The following Table XXXII shows the results obtained:

TABLE XXXII

| Sample | L | a | b |
|---|---|---|---|
| PMM-derived CPI | 81.64 | −1.46 | 29.57 |
| Supernatant-derived CPI | 81.24 | −0.76 | 21.15 |

Example 10

This Example illustrates the use of an antioxidant and adsorbent in the extraction step.

Bench scale experiments were carried out in which samples of commercial canola oil seed meal which had been desolventized at 100° C. were extracted with 0.15 M NaCl for 30 minutes at a concentration of 15 wt %. Extractions were effected with and without the addition of Polyclar Super R at varying levels, namely 0.5 wt %, 1.0 wt %, 1.5 wt %, 2.0 wt %, 2.5 wt %, 3.0 wt %, 4.0 wt % and 5.0 wt % and with and without the addition of 0.5 wt % ascorbic acid. Following the extraction, the solutions were centrifuged and then analyzed for phenolics content (A330 absorbance), visible colour (A420 absorbance) and protein content.

The results obtained with and without ascorbic acid are set forth in Table XXXIII and XXXIV respectively:

TABLE XXXIII

| % w/v Polyclar | A330 | A420 | Protein g/L |
|---|---|---|---|
| Control | 96.2 | 2.8 | 24.6 |
| 1.0% Polyclar | 93.0 | 3.3 | 25.8 |
| 1.5% Polyclar | 71.7 | 2.65 | 26.1 |
| 2.0% Polyclar | 63.0 | 2.01 | 23.5 |
| 2.5% Polyclar | 72.4 | 2.54 | 26.4 |
| 3.0% Polyclar | 64.7 | 2.63 | 26.4 |

TABLE XXXIII-continued

| % w/v Polyclar | A330 | A420 | Protein g/L |
|---|---|---|---|
| 4.0% Polyclar | 63.0 | 2.41 | 28.0 |
| 5.0% Polyclar | 61.6 | 2.39 | 25.9 |

TABLE XXXIV

| % w/v Polyclar | A330 | A420 | Protein g/L |
|---|---|---|---|
| Control | 90.5 | 3.12 | 25.9 |
| 1.0% Polyclar | 82.7 | 2.22 | 28.4 |
| 1.5% Polyclar | 90.6 | 2.59 | 32.8 |
| 2.0% Polyclar | 83.5 | 2.32 | 26.8 |
| 2.5% Polyclar | 80.2 | 2.09 | 27.1 |
| 3.0% Polyclar | 68.1 | 2.25 | 26.5 |
| 4.0% Polyclar | 66.5 | 2.62 | 29.9 |
| 5.0% Polyclar | 52.4 | 1.73 | 26.0 |

As may be seen from the results set forth in the Tables XXXIII and XXXIV, significant reduction in both A330 and A420 were obtained in the presence of Polyclar both with and without the presence of ascorbic acid. A 2.5% w/v concentration of Polyclar achieved a 25% reduction in the A330 and an 11% reduction in the A420 seen in the control, when no ascorbic acid was added to the extraction. Higher levels of Polyclar further reduced the A330 and A420 values. With ascorbic acid present during the extraction, a 12% reduction in A330 and 34% reduction in A420 were seen when 2.5% w/v of Polyclar was used. The protein content of the solution was unaffected by the presence or absence of the Polyclar.

Example 11

This Example illustrates the effect of ethanol washing of canola oil seed meal on colour.

10 g samples of dehulled canola oil seed meal were mixed with 100 ml of ethanol and allowed to mix for 30 minutes at 45° C., 40° C. and room temperature, which was regulated with a circulating water bath and a jacketed vessel.

After the 30 minutes mixing period, the meal/solvent slurry was poured through a filter to separate the meal from the extracts. The procedure was repeated until no more colour was removed or until the A330 and A420 absorbance readings began to plateau. The meal from each solvent wash/extraction step was dried and 0.15 M NaCl protein extractions at ambient temperature for 30 minutes were performed.

UV absorbance of the extract solution was performed for each extract sample. Tables XXXV, XXXVI and XXXVII show the A330 and A420 values for the extraction done at room temperature, 40° C. and 45° C., respectively:

TABLE XXXV

| Room temperature Ethanol Extraction | | |
|---|---|---|
| | A330 | A420 |
| $1^{st}$ Solvent Extraction | 34.3 | 0.494 |
| $2^{nd}$ Solvent Extraction | 12.8 | 0.232 |
| $3^{rd}$ Solvent Extraction | 6.1 | 0.100 |
| $4^{th}$ Solvent Extraction | 2.8 | 0.047 |
| $5^{th}$ Solvent Extraction | 2.3 | 0.045 |
| $6^{th}$ Solvent Extraction | 1.7 | 0.040 |

TABLE XXXVI

| 40° C. Ethanol Extraction | | |
|---|---|---|
| | A330 | A420 |
| $1^{st}$ Solvent Extraction | 30.9 | 0.528 |
| $2^{nd}$ Solvent Extraction | 20.1 | 0.257 |
| $3^{rd}$ Solvent Extraction | 9.3 | 0.139 |
| $4^{th}$ Solvent Extraction | 7.01 | 0.108 |
| $5^{th}$ Solvent Extraction | 4.74 | 0.073 |
| $6^{th}$ Solvent Extraction | 6.66 | 0.063 |
| $7^{th}$ Solvent Extraction | 3.69 | 0.035 |
| $8^{th}$ Solvent Extraction | 2.57 | 0.031 |
| $9^{th}$ Solvent Extraction | 2.6 | 0.037 |
| $10^{th}$ Solvent Extraction | 2.4 | 0.033 |

TABLE XXXVII

| 45° C. Ethanol Extraction | | |
|---|---|---|
| | A330 | A420 |
| $1^{st}$ Solvent Extraction | 43.0 | 0.610 |
| $2^{nd}$ Solvent Extraction | 21.0 | 0.301 |
| $3^{rd}$ Solvent Extraction | 14.6 | 0.191 |
| $4^{th}$ Solvent Extraction | 7.83 | 0.129 |
| $5^{th}$ Solvent Extraction | 7.65 | 0.105 |
| $6^{th}$ Solvent Extraction | 7.34 | 0.092 |
| $7^{th}$ Solvent Extraction | 5.76 | 0.086 |
| $8^{th}$ Solvent Extraction | 6.04 | 0.063 |
| $9^{th}$ Solvent Extraction | 4.89 | 0.065 |
| $10^{th}$ Solvent Extraction | 4.98 | 0.052 |

As may be seen from this data, solvent extraction at lower temperature did not remove as many colour and phenolic compounds as temperatures in the 40° to 45° C. range, with the room temperature extraction ceasing to remove contaminants after only 6 extractions while the higher temperature extraction each removed contaminants until the $10^{th}$ extraction.

The protein content and at absorbance 330 nm and 420 nm of the protein extract solutions were determined and the results appear in the following Table XXXVIII:

TABLE XXXVIII

| | A330 | A420 | % Protein |
|---|---|---|---|
| Control Ext. | 97.8 | 2.84 | 1.92 |
| Room temperature | 78.4 | 2.57 | 2.01 |
| 40° C. | 60.1 | 1.97 | 2.23 |
| 45° C. | 58.2 | 2.29 | 1.79 |

As may be seen from this Table, protein loss can be avoided while approximately 40% of the phenolic compounds and 30% of the A420 absorbing material are removed by pre-extracting the meal with ethanol at 40° C.

Example 12

This Example illustrates the preparation of a canola protein isolate with ethanol extraction of meal.

Eleven 600 g aliquots of dehulled oil seed meal were subjected to four 3 L ethanol extractions using a meal to ethanol w/v ratio of 1:5. The extractions were done for 30 minutes at 35° C.

Following the 30 minute mixing time, the slurry was allowed to settle and the supernatant was poured off. UV absorbances at A330 and A420 were determined for each extraction and a protein content measurement was carried out on the first extraction from the first aliquot of meal extracted.

Following the fourth extraction, the meal was spread out in a shallow pan in a fume hood and allowed to dry overnight. The entire batch of washed meal was allowed to desolventize in the fume hood for one more night before the 5.4 kg of dried extracted meal was used in a 50 L batch extraction.

With each extraction of the sample, the colour of the supernatant became progressively lighter and A330 and A420 decreased. On average, a 5-fold reduction in A330 and a 6-fold reduction in A420 was seen. The absorbance values are A420 and A330 respectively for the various extracts are set forth in the following Tables XXXIX and XL:

TABLE XXXIX

Absorbance at A420

| Meal Aliquot | Extract 1 | Extract 2 | Extract 3 | Extract 4 |
| --- | --- | --- | --- | --- |
| A | 1.688 | 0.606 | 0.276 | 0.181 |
| B | 0.87 | 0.379 | 0.124 | 0.103 |
| C | 0.891 | 0.432 | 0.206 | 0.129 |
| D | 0.182 | 0.334 | 0.218 | 0.116 |
| E | 0.8 | 0.366 | 0.159 | 0.093 |
| F | 0.896 | 0.469 | 0.215 | 0.114 |
| G | 0.8 | 0.398 | 0.194 | 0.122 |
| H | 0.821 | 0.376 | 0.203 | 0.117 |
| I | 0.836 | 0.398 | 0.189 | 0.111 |
| J | 0.827 | 0.375 | 0.203 | 0.131 |
| K | 0.833 | 0.402 | 0.265 | 0.115 |

TABLE XL

Absorbance at A330

| Meal Aliquot | Extract 1 | Extract 2 | Extract 3 | Extract 4 |
| --- | --- | --- | --- | --- |
| A | 98.1 | 47.5 | 22.1 | 12.8 |
| B | 30.7 | 14.7 | 13.9 | 10.43 |
| C | 61.2 | 27.8 | 15.3 | 10.9 |
| D | 57.5 | 25.3 | 19.5 | 11.37 |
| E | 60.4 | 27.7 | 16.2 | 10.4 |
| F | 58.6 | 29.3 | 18.4 | 11.4 |
| G | 58.8 | 28.6 | 17.3 | 12 |
| H | 57.9 | 26.3 | 14.3 | 10.02 |
| I | 60.1 | 29.3 | 15.6 | 11.02 |
| J | 56.7 | 30.1 | 17.8 | 10.89 |
| K | 61.2 | 27.98 | 14.77 | 11.08 |

The 5 kg of ethanol-extracted meal was added to 50 L of 0.15 M NaCl and mixed for 30 minutes at a room temperature of 20° C. with 0.05 wt % ascorbic acid added to the slurry after 15 minutes as an antioxidant.

The residual canola meal was removed and washed on a vacuum filter belt. The resulting protein solution was clarified by filtration through a 20 μm bag filter followed by centrifugation at 6500 rpm for 5 minutes to produce 39.6 L of protein solution having a protein content of 23.7 g/L.

37.55 L of the clarified protein solution was concentrated to 3 L using an ultrafiltration system using 10,000 dalton molecular weight cut-off membranes. The concentrated protein solution was diafiltered on a diafiltration system using 10,000 dalton molecular weight cut-off membranes using 24 L (=8 retentate volumes) of 0.15 M NaCl containing 0.05 wt % ascorbic acid. The resulting 3L of concentrated and diafiltered canola protein solution had a protein content of 184 g/L.

The concentrated and diafiltered solution at 30° C. was diluted into 30 L of water having a temperature of 4° C. A white cloud of protein micelles formed immediately and was allowed to settle. The supernatant was removed and the precipitated, viscous, sticky mass (PMM) (5.78 kg) was removed from the bottom of the vessel and spray dried. The dried protein isolate had a protein content of 101.2 wt % (N×6.25) d.b.

26 L of supernatant from the micelle formation was concentrated to 3 L by concentration on an ultrafiltration system using 10,000 dalton molecular weight cut-off membranes. The concentrated supernatant then was diafiltered on a diafiltration system using 10,000 dalton molecular weight cut-off membranes with 6 L of water.

The concentrated and diafiltered solution was dried and the dried protein was found to have a protein content of 101.3 wt % (N×6.25) d.b.

Samples of the PMM-derived canola protein isolate (CPI) and the supernatant derived canola protein isolate were analyzed for lightness (L) and chromaticity (a and b) using a Minolta R-310 colorimeter. The following Table XLI shows the results obtained:

TABLE XLI

| Sample | L | a | b |
| --- | --- | --- | --- |
| PMM-derived CPI | 84.32 | −1.84 | 23.85 |
| Supernatant-derived CPI | 81.92 | −0.5 | 14.18 |

These products were quite light with 'a' and 'b' values suggesting relatively lower levels of red and yellow colour rotes.

SUMMARY OF DISCLOSURE

In summary of this disclosure, the present invention provides with the recovery of canola protein isolates having decreased colour, by effecting one or more operations during isolate preparation designed to remove colourant-causing components, inhibition of oxidation of colourant-causing components and the removal of colourants. Modifications are possible within the scope of the invention.

What we claim is:

1. A process of forming a canola protein isolate, comprising:
    processing canola seeds to form a canola protein meal,
    extracting the canola protein meal to form an aqueous canola protein solution,
    concentrating the aqueous canola protein solution to form a concentrated aqueous canola protein solution,
    recovering a canola protein isolate from said concentrated aqueous canola protein solution by adding the concentrated aqueous solution to chilled water to form a protein micellar mass, and separating the protein micellar mass from supernatant,
    processing said supernatant to recover additional canola protein isolate therefrom by concentrating the supernatant, subjecting the concentrated supernatant to diafiltration and recovering canola protein isolate from the diafiltered supernatant,
    wherein at least one process step during said process results in a canola protein isolate having a decreased color.

2. The process of claim 1, wherein said processing of canola seeds comprises inactivation of myrosinase in the canola oil seeds.

3. The process of claim 1, wherein said extraction step is effected on low temperature desolventized meal or air desolventized meal.

4. The process of claim 1, wherein said concentrated aqueous canola protein solution is subjected to diafilteration prior to adding to chilled water.

5. The process of claim 1, wherein said at least one process step comprises solvent extracting said canola protein meal with an alcohol.

6. The process of claim 1 wherein said at least one process step comprises solvent extracting said canola protein isolate with an aqueous alcoholic solution.

* * * * *